US012642908B2

(12) United States Patent
Hu et al.

(10) Patent No.: US 12,642,908 B2
(45) Date of Patent: Jun. 2, 2026

(54) FLUID DELIVERY MECHANISM AND NUTRIENT PUMP

(71) Applicant: Medcaptain Medical Technology Co., Ltd., Shenzhen (CN)

(72) Inventors: Pan Hu, Shenzhen (CN); Xiang Li, Shenzhen (CN); Zhiwu Deng, Shenzhen (CN)

(73) Assignee: Medcaptain Medical Technology Co., Ltd., Shenzhen (CN)

( * ) Notice: Subject to any disclaimer, the term of this patent is extended or adjusted under 35 U.S.C. 154(b) by 0 days.

(21) Appl. No.: 18/915,257

(22) Filed: Oct. 14, 2024

(65) Prior Publication Data

US 2025/0135096 A1 May 1, 2025

(30) Foreign Application Priority Data

Oct. 27, 2023 (CN) .......................... 202311416442.X
Oct. 27, 2023 (CN) .......................... 202311417700.6

(51) Int. Cl.
| | |
|---|---|
| *A61M 5/14* | (2006.01) |
| *A61M 5/142* | (2006.01) |
| *A61M 60/279* | (2021.01) |
| *A61M 60/284* | (2021.01) |
| *F04B 43/12* | (2006.01) |
| *F04B 53/10* | (2006.01) |

(52) U.S. Cl.
CPC ...... *A61M 5/1408* (2013.01); *A61M 5/14232* (2013.01); *A61M 60/279* (2021.01); *A61M 60/284* (2021.01); *F04B 43/1238* (2013.01);

*F04B 43/1261* (2013.01); *F04B 43/1269* (2013.01); *F04B 53/10* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,108,167 A | * | 8/1978 | Hickman | ................ F04B 17/03 |
| | | | | 601/162 |
| 4,445,826 A | * | 5/1984 | Tarr | ........................ F04B 19/20 |
| | | | | 417/512 |
| 5,584,671 A | * | 12/1996 | Schweitzer, Jr. | ..... A61M 5/142 |
| | | | | 604/151 |
| 7,846,131 B2 | * | 12/2010 | Hudson | ............. A61M 5/14232 |
| | | | | 604/32 |

(Continued)

FOREIGN PATENT DOCUMENTS

| | | |
|---|---|---|
| CN | 102908252 A | 2/2013 |
| CN | 109846716 A | 6/2019 |

(Continued)

*Primary Examiner* — Binh Q Tran
(74) *Attorney, Agent, or Firm* — Anova Law Group, PLLC

(57) ABSTRACT

The invention provides a fluid delivery mechanism and a nutrient pump, the fluid delivery mechanism including a delivery assembly and a connecting base. The delivery assembly includes a flow path and a valve mechanism provided on the flow path, and the delivery assembly is mounted on the connecting base. The fluid delivery mechanism provided by the invention is reliably connected, thereby effectively controlling the fluid conduction or cutoff of the infusion assembly and preventing the occurrence of free-flow phenomenon.

18 Claims, 7 Drawing Sheets

(56)             References Cited

U.S. PATENT DOCUMENTS

| | | | |
|---|---|---|---|
| 2007/0135766 A1* | 6/2007 | Fournie | A61J 15/0092 |
| | | | 604/131 |
| 2011/0319836 A1* | 12/2011 | Lee | F16K 11/0856 |
| | | | 604/248 |
| 2016/0151566 A1* | 6/2016 | Magers | A61M 5/16813 |
| | | | 604/152 |
| 2020/0041021 A1* | 2/2020 | Moss | A61M 1/154 |
| 2022/0031942 A1 | 2/2022 | Song et al. | |
| 2022/0378666 A1* | 12/2022 | Beck | A61M 5/1413 |

FOREIGN PATENT DOCUMENTS

| | | |
|---|---|---|
| CN | 210114674 U | 2/2020 |
| CN | 210170672 U | 3/2020 |
| CN | 111467242 A | 7/2020 |
| CN | 112259975 A | 1/2021 |
| CN | 214713485 U | 11/2021 |
| CN | 214762291 U | 11/2021 |
| CN | 216251498 U | 4/2022 |
| CN | 116877543 A | 10/2023 |

* cited by examiner

FLUID DELIVERY MECHANISM AND NUTRIENT PUMP

REFERENCE TO RELATED APPLICATIONS

The invention claims priority of Chinese Patent Application No. 202311417700.6, entitled "Fluid delivery mechanism and Nutrient Pump" filed with the China National Intellectual Property Administration on Oct. 27, 2023 and Chinese Patent Application No. 202311416442.X, entitled "Nutrient Pump" filed with the China National Intellectual Property Administration on Oct. 27, 2023, all of which are incorporated herein by reference in their entirety.

TECHNICAL FIELD

This invention generally relates to the technical field of medical devices, and more particularly, to a fluid delivery mechanism and nutrient pump.

BACKGROUND ART

Nutrient pump is a nutrient infusion pump for nasal feeding, which can improve the nutritional status of patients by feeding water, nutrient fluid and homemade rice milk of a certain concentration to patients through the nasal feeding tube.

The nutrient pump includes a nutrient pump main body and an infusion tube assembled to the nutrient pump main body. The infusion tube is filled with a fluid such as a nutrient fluid or a cleaning fluid, and the infusion tube is assembled to the nutrient pump main body. The nutrient pump main body provides a driving force to the infusion tube to propel the fluid in the infusion tube forward so as to deliver the nutrient fluid and the other fluids to the patient through the nasal feeding tube.

However, in existing nutrient pumps, the nutrient pump main body is unable to effectively control the fluid conduction or cutoff state of the infusion tube.

SUMMARY OF THE INVENTION

In order to solve at least one problem mentioned in the background art, the invention provides a fluid delivery mechanism and a nutrient pump, where the fluid delivery mechanism is reliably connected, thereby effectively controlling the fluid conduction or cutoff of the infusion assembly and preventing the occurrence of a free-flow phenomenon.

One aspect of the invention provides a fluid delivery mechanism comprising:

a delivery assembly comprising a flow path and a valve mechanism provided in the flow path; and a connecting base, the delivery assembly being mounted on the connecting base;

wherein the valve mechanism comprises a valve housing and a valve core removably connected to the valve housing; the valve housing comprises an outlet and at least one inlet; a first opening and a second opening on a circumference of the valve core, and the valve core defines a fluid passage with the valve housing; the fluid passage is in communication with the first opening, the second opening, and the outlet of the valve housing;

wherein the valve core is rotatable in a first direction to make one of the first opening and the second opening in communication with one of the at least one inlet.

In a possible embodiment, the at least one inlet comprises a first inlet and a second inlet; the valve core is rotatable in a first direction to bring the first inlet into communication with the first opening and rotatable in a second direction to bring the second inlet into communication with the second opening, wherein the first direction is opposite to the second direction.

In one possible embodiment, the first inlet and the second inlet are disposed side by side on the valve housing; when the valve core is in an initial position, the first opening is disposed on a side of the first inlet away from the second inlet, and the second opening is disposed on a side of the second inlet away from the first inlet.

In one possible embodiment, the valve core is provided with a reversing groove.

In one possible embodiment, the delivery assembly further comprises an outlet tube and at least one inlet tube, wherein each of the at least one inlet tube is connected to a corresponding inlet on the valve mechanism and the fluid outlet tube is connected to the outlet of the valve mechanism.

In one possible embodiment, the connecting base is provided with a first locking structure, and the valve mechanism is detachably connected to the first locking structure.

In one possible embodiment, the delivery assembly further comprises a tube connector, wherein the tube connector is provided on the flow path, the connecting base is provided with a second locking structure, and the tube connector is detachably connected to the second locking structure.

In one possible embodiment, the connecting base is further provided with a first positioning structure and/or a second positioning structure.

In one possible embodiment, the connecting base is further provided with an identification member.

Another aspect of the invention provides a nutrient pump comprising a pump main body and any one of the above-mentioned fluid delivery mechanisms, wherein the fluid delivery mechanism is detachably connected to the pump main body.

In one possible embodiment, the pump main body is provided with a switching member, and the switching member is capable of extending into a reversing groove of the valve core of the valve mechanism to drive the valve core.

In one possible embodiment, the pump main body is provided with an anti-disconnecting member, and the anti-disconnecting member is movable to a locked position or an unlocked position;

when the anti-disconnecting member is in the locked position, the anti-disconnecting member is connected to the connecting base; when the anti-disconnecting member is in the unlocked position, the anti-disconnecting member is disengaged from the connecting base.

In a possible embodiment, the pump main body is provided with a fixing structure, and the fixing structure is detachably connected to a second positioning structure of the connecting base.

In one possible embodiment, the pump main body is provided with a detecting member, and the connecting base is provided with an identification member; the detecting member is cooperated with the identification member to detect an installation state of the connecting base.

Another aspect of the invention provides a nutrient pump comprising a pump main body, and a first driving mechanism, a switching member and an anti-disconnecting member provided on the pump main body;

the first driving mechanism is connected to the switching member to drive the switching member to move between at least two positions to control a fluid conduction cut-off state of a fluid delivery mechanism; and the first driving mechanism is connected to the anti-disconnecting member to drive the anti-disconnecting member to move between at least two positions.

In one possible embodiment, the first driving mechanism comprises a first driving member, and the first driving member is configured to drive both the switching member and the anti-disconnecting member to move.

In one possible embodiment, the first driving mechanism further comprises a first transmission assembly; the first transmission assembly is connected to the first driving member in a transmission mode, and the switching member and the anti-disconnecting member are both connected to an output end of the first transmission assembly.

In one possible embodiment, the first transmission assembly comprises a first transmission member and a second transmission member, the switching member is connected to an output end of the first transmission member, and the anti-disconnecting member is connected to an output end of the second transmission member.

In one possible implementation, the first transmission member is a gear or rack structure, and the second transmission member is a gear or rack structure.

In one possible embodiment, the first driving mechanism further comprises a worm structure; the worm structure is connected to the first driving member in a transmission mode, and the first driving member and the second driving member are both engaged with the worm structure; or one of the first driving member and the second driving member is engaged with the worm structure, and the first driving member is engaged with the second driving member.

In one possible embodiment, the first driving mechanism further comprises a reducer, and the first driving member is connected to the worm structure through the reducer.

In one possible embodiment, the first driving mechanism comprises two first driving members, one of the two first driving members is connected to the switching member, and the other of the two first driving members is connected to the anti-disconnecting member.

In one possible embodiment, the pump main body is further provided with a second driving mechanism, and the second driving mechanism is configured to drive the pump roller to rotate.

In one possible embodiment, the second driving mechanism comprises a second driving member and a second transmission assembly that are connected to each other in a transmission mode, and an output end of the second transmission assembly extends outside the pump main body.

In one possible embodiment, the nutrient pump further comprises a pump roller, and the pump roller is connected to the output end of the second transmission assembly.

In one possible embodiment, the nutrient pump further comprises a fluid delivery mechanism, and the fluid delivery mechanism is detachably connected to the pump main body; the fluid delivery mechanism comprises a control valve and a connecting base that are connected to each other, the switching member is configured to switch an conduction state of the control valve, and the anti-disconnecting member is configured to be removably connected to the connecting base.

In one possible embodiment, the at least two positions of the switching member comprise a conduction position and a cut-off position, and the at least two positions of the anti-disconnecting member comprise a locked position and an unlocked position;

when the switching member is in the conduction position, the anti-disconnecting member is in the locked position; when the switching member is in the cut-off position, the anti-disconnecting member is in the unlocked position.

The invention provides a fluid delivery mechanism and a nutrient pump, the fluid delivery mechanism includes a delivery assembly and a connecting base. As a main functional component of the fluid delivery mechanism, the delivery assembly is provided with a flow path for the fluid to pass through. A valve mechanism is provided on the flow path, and the valve mechanism has a function of switching the fluid path and automatically blocking the fluid path. The delivery assembly is mounted on the connecting base, and the fluid delivery mechanism is detachably mounted on the nutrient pump through the connecting base. The delivery assembly is mounted on the connecting base, and the fluid delivery mechanism is detachably mounted on the nutrient pump through the connector. The delivery assembly is fixed on the connecting base, which can prevent the fluid delivery mechanism from falling off abnormally from the nutrient pump and ensure the normal operation of the nutrient pump. The valve mechanism and the connecting base can work together to prevent the delivery assembly from free-flowing phenomenon, so as to avoid causing harm to the patient.

BRIEF DESCRIPTION OF THE DRAWINGS

In order to more clearly illustrate the technical solutions in the embodiments or prior art of the invention, the accompanying drawings to be used in the description of the embodiments or prior art will be briefly introduced below. Obviously, the accompanying drawings in the following description are some embodiments of the invention. For a person of ordinary skill in the art, other accompanying drawings may be obtained from these accompanying drawings without creative labor.

DESCRIPTION OF THE REFERENCE SIGNS

Figure 1:
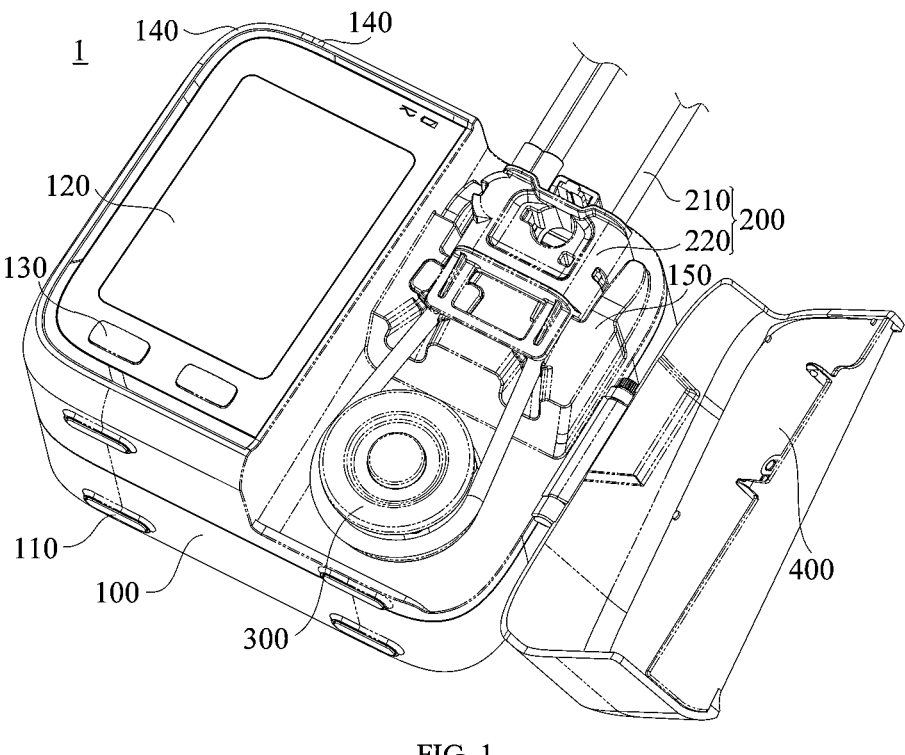
FIG. 1 shows a schematic structural diagram of a nutrient pump provided by embodiments of the invention.

1—nutrient pump;

100—pump main body; 200—fluid delivery mechanism; 300—roller; 400—pump door;

110—support pad; 120—display; 130—button; 140—indicator light; 150—support base; 160—switching member; 170—anti-disconnecting member; 180—snap base; 210—delivery assembly; 220—connecting base; 500—first driving mechanism; 600—second driving mechanism;

151—accommodation groove; 171—main rod; 172—locking rod; 181—slot; 211—valve mechanism; 212—fluid inlet tube; 213—fluid outlet tube; 214—connecting tube; 215—tube connector; 221—main body portion; 222—pressing plate; 531—first transmission member; 532—second transmission member; 621—first gear; 622—second gear; 623—third gear;

1511—bubble sensor; 1512—pressure sensor; 2101—snap fastener; 2111—valve housing; 2112—valve core; 2121—first fluid inlet tube; 2122—second fluid inlet tube; 2211—first limit groove; 2212—second limit groove; 2213—positioning groove; 2214—resilient snap; 2215—mounting groove;

21111—inlet; 21112—outlet; 21113—first recess groove; 21121—reversing groove; 21122—first opening; 21123—second opening; 21124—fluid passage; 21125—limit structure; 22101—limit strip; 22102—snap slot; 22131—anti-disconnecting hole; 22141—tab; 22142—stop portion; 22151—identification member;

21111*a*—first inlet; 21111*b*—second inlet.

DETAILED DESCRIPTION

Improving the nutritional status of patients is the basic condition of disease treatment. Clinical nutrition is divided into enteral nutrition and parenteral nutrition, while enteral nutrition is more conducive to the metabolism and utilization of physiological nutrients in the human body, and it can safely and effectively promote and maintain the intact structure and function of the gastrointestinal tract, thereby protecting the gastric mucous barrier, reducing the number of complications, and lowering the cost of treatment.

In clinical practice, the nutrient pump (also known as enteral nutrient pump) is generally used to deliver water, nutrient solution and homemade rice milk of a certain concentration to the patient to provide nutrition for the patient. The nutrient pump typically includes a nutrient pump main body and an infusion assembly assembled on the nutrient pump main body. The nutrient pump main body provides a driving force for the infusion assembly to propel the fluid within the tubing of the infusion assembly forward so as to deliver the nutrient fluid, the cleaning fluid, and other fluids to the patient.

However, in existing nutrient pumps, the infusion assembly is not securely connected to the nutrient pump main body, and is prone to abnormal dislodgement from the nutrient pump main body, which affects the normal operation of the nutrient pump, and can lead to free-flow phenomena of the infusion assembly, which may cause injury to the patient.

In view of this, embodiments of the invention provide a fluid delivery mechanism and a nutrient pump, the fluid delivery mechanism includes a delivery assembly and a connecting base. As a main functional component of the fluid delivery mechanism, the delivery assembly is provided with a flow path for the fluid to pass through. A valve mechanism is provided on the flow path, and the valve mechanism has a function of switching the fluid path and automatically blocking the fluid path. The delivery assembly is mounted on the connecting base, and the fluid delivery mechanism is detachably mounted on the nutrient pump through the connecting base. The delivery assembly is mounted on the connecting base, and the fluid delivery mechanism is detachably mounted on the nutrient pump through the connector. The delivery assembly is fixed on the connecting base, which can prevent the fluid delivery mechanism from falling off abnormally from the nutrient pump and ensure the normal operation of the nutrient pump. The valve mechanism and the connecting base can work together to prevent the delivery assembly from free-flowing phenomenon, so as to avoid causing harm to the patient.

In order to make the object, technical solutions and advantages of the embodiments of the invention clearer, the technical solutions in the embodiments of the invention will be described clearly and completely in the following in conjunction with the accompanying drawings in the embodiments of the invention. Obviously, the described embodiments are a part of the embodiments of the invention and not all of the embodiments. Based on the embodiments in this application, all other embodiments obtained by a person of ordinary skill in the art without making creative labor fall within the scope of protection of this application.

Figure 2:
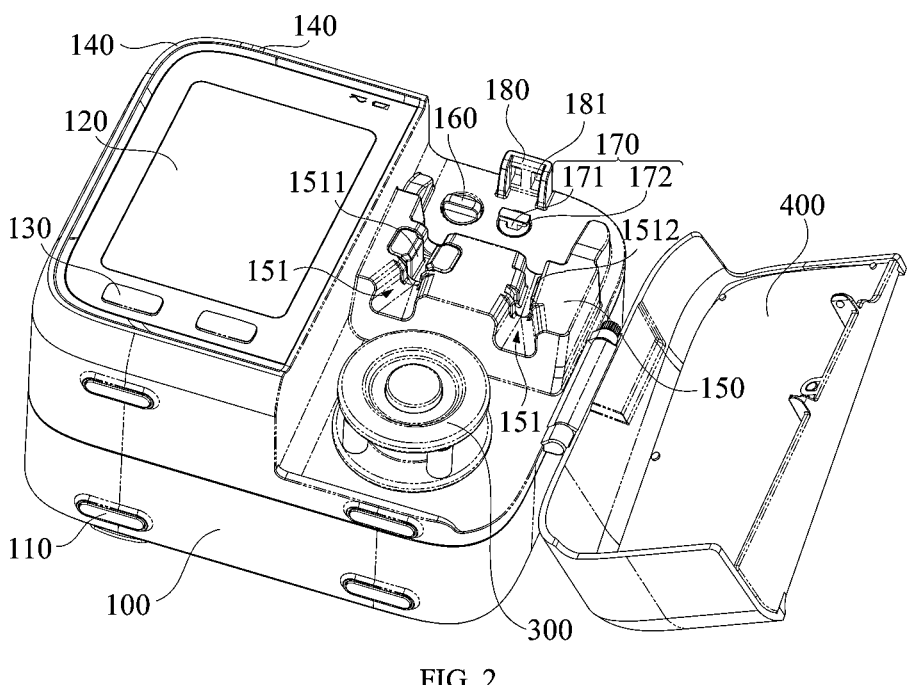
FIG. 2 shows a schematic structural diagram of the nutrient pump of FIG. 1 after removal of the fluid delivery mechanism.

FIG. 1 shows a schematic structural diagram of the nutrient pump provided by embodiments of the invention; FIG. 2 shows a schematic structural diagram of the nutrient pump of FIG. 1 after removal of the fluid delivery mechanism.

As shown in FIGS. 1 and 2, an embodiment of the invention provides a nutrient pump 1. The nutrient pump 1 includes a pump main body 100, a fluid delivery mechanism 200, a roller 300, and a pump door 400. The pump main body 100 is the main structure of the nutrient pump 1, the fluid delivery mechanism 200 and the roller 300 are detachably mounted on the pump main body 100, and the pump door 400 is movably connected to the pump main body 100.

One side surface of the pump main body 100 may be an operating surface, and an operator may face the operating surface of the pump main body 100 to operate the pump main body 100. The fluid delivery mechanism 200 and the roller 300 may be mounted on the operating surface of the pump main body 100, and the pump door 400 may be covered on the operating surface of the pump main body 100.

As an example, the pump main body 100 may be erected on a support base such as a tabletop and a support frame, and a flexible support pad 110 may be provided on the bottom surface of the pump main body 100 to avoid hard contact between the pump main body 100 and the support base, to increase friction between the pump main body 100 and the support base, thereby ensuring the stability of the pump main body 100, and slowing down the abrasion or scuffing of the bottom surface of the pump main body 100. One side of the pump main body 100 may be an operating surface, and the operating surface may, for example, be perpendicular to the bottom surface.

As shown in FIGS. 1 and 2, one side of the operating surface of the pump main body 100 may be a display control area, and the other side may be an accessory mounting area. The display control area is mainly configured to display information related to the pump main body 100, and an operator may operate in the display control area to control the operating state of the pump main body 100. The accessory installation area is configured to install some accessories with the pump main body 100, which together with the pump main body 100 form the nutrient pump 1 to realize the function of the nutrient pump 1 to transport nutrients.

The display control area may be provided with a display 120, buttons 130, and indicator lights 140. The display 120 may occupy a large portion of the display control area, the buttons 130 and the indicator lights 140 may be provided on the peripheral side of the display 120. The display 120 is configured to display information such as operating parameters and function options of the nutrient pump 1. The buttons 130 may include an on/off button, and a return button. The indicator light 140 may include an operating indicator light 140, and an alarm indicator light 140.

The aforementioned fluid delivery mechanism 200 and roller 300 may be mounted in the accessory mounting area, and the pump door 400 may be rotatably attached to the side wall of the pump main body 100, and located on a side where the accessory mounting area is located. The pump door 400 may cover only the accessory mounting area to protect the accessories mounted on the accessory mounting area, while the display control area is exposed outside the pump door 400 to facilitate an operator's observation of the display 120 and operation of the pump main body 100. As an example, the pump door 400 may be a transparent member so that the operating status of the accessories in the accessory mounting area can be observed through the pump door 400 to facilitate real-time observation of the operating status of the nutrient pump 1.

As shown in FIGS. 1 and 2, the piping of the fluid delivery mechanism 200 may be disposed around the outer periphery of the roller 300, and the roller 300 exerts a certain pressure on the piping of the fluid delivery mechanism 200, so that the piping of the fluid delivery mechanism 200 is in a state of being stretched. The pump main body 100 may be provided with a driving device, and a driving force of the driving device may be transmitted to the roller 300, and the roller 300 rotates under the drive of the driving device.

When the driving device drives the roller 300 to rotate, the roller 300 generates a pushing force on the fluid within the piping of the fluid delivery mechanism 200, pushing the fluid within the piping of the fluid delivery mechanism 200 to flow along the piping to deliver the nutrient within the fluid delivery mechanism 200 to the patient. When the roller 300 stops rotating, the piping of the fluid delivery mechanism 200 is subjected to a higher pressure from the roller 300, the fluid path within the piping is equivalent to being blocked, and the fluid within the piping stops continuing to flow forward, then the nutrient pump 1 stops delivering the nutrient to the patient.

A support base 150 may also be mounted in the accessory mounting area on the operating surface of the pump main body 100, and the support base 150 is configured to restrict the piping of the fluid delivery mechanism 200. For example, the support base 150 may be provided with an accommodation groove 151, and the piping of the fluid delivery mechanism 200 may be disposed in the accommodation groove 151, so as to restrict the fluid delivery mechanism 200 and limit the extension direction of the piping of the fluid delivery mechanism 200, which helps to make the piping of the fluid delivery mechanism 200 more smoothly disposed around the periphery of the roller 300.

The following is a detailed description of a connection structure between the fluid delivery mechanism 200 and the pump main body 100.

Figures 3, 4:
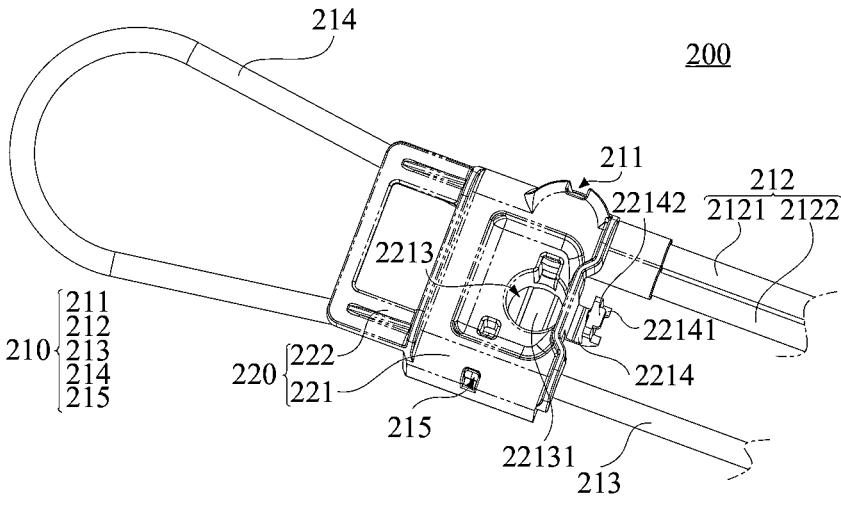
FIG. 3 shows a schematic structural diagram of a fluid delivery mechanism in one view provided by embodiments of the invention.
FIG. 4 shows a schematic structural diagram of the fluid delivery mechanism in FIG. 3 in another view.

FIG. 3 shows a schematic structural diagram of a fluid delivery mechanism in one view provided by embodiments of the invention, and FIG. 4 shows a schematic structural diagram of the fluid delivery mechanism in FIG. 3 in another view.

As shown in FIG. 3 or FIG. 4, the fluid delivery mechanism 200 includes a delivery assembly 210 and a connecting base 220. The delivery assembly 210 is a main functional component of the fluid delivery mechanism 200, and the delivery assembly 210 is formed with a flow path for fluid passage inside the delivery assembly 210 in order to deliver to the patient a fluid-like nutrient such as the aforementioned water, nutrient solution, and homemade meal milk of a certain concentration. The delivery assembly 210 is mounted on the connecting base 220, and removably connected to the pump main body 100 to secure the fluid delivery mechanism 200 to the pump main body 100.

By mounting the delivery assembly 210 on the connecting base 220 and utilizing the connecting base 220 to secure the delivery assembly 210 to the pump main body 100, the delivery assembly 210 can be prevented from falling off of the pump main body 100 abnormally. For example, it prevents the delivery assembly 210 from falling off the pump main body 100 during delivery of nutrients to a patient, so as to avoid affecting, the normal operation of the nutrient pump 1 due to the abnormal falling off of the delivery assembly 210. Furthermore, it prevents unintended gravity infusion of fluid within the delivery assembly 210 due to free-flow, so as not to cause harm to the patient as a result.

Moreover, for the delivery assembly 210 formed by the connection of the flexible hose, the connecting base 220 protects the flexible hose, so as to enhance the structural strength of the fluid delivery mechanism 200, and support and position the delivery assembly 210, which helps to maintain a certain shape configuration of the delivery assembly 210. It facilitates the setting of the piping of the delivery assembly 210 on the roller 300, and is conducive to maintaining the delivery assembly 210 in the state of being connected with the roller 300, so as to prevent the piping of the delivery assembly 210 from detaching from the roller 300.

The delivery assembly 210 is provided with a valve mechanism 211, which is provided on the flow path of the delivery assembly 210. The valve mechanism 211 may be controlled to rotate by the pump main body 100 in order to change the connectivity state of the flow path in the delivery assembly 210. For example, the valve mechanism 211 may be in the state of connecting the flow path, or it may be in the state of cutting off the flow path. When the delivery assembly 210 has more than two flow paths, the valve mechanism 211 may also switch between different flow paths.

In this way, on the basis of fixing the delivery assembly 210 to the pump main body 100 by means of the connecting base 220, and the valve mechanism 211 may also be used to prevent a free-flow phenomenon of the fluid in the delivery assembly 210. For example, when the delivery assembly 210 is detached from the pump main body 100, the valve mechanism 211 can be rotated to a state that cuts off the flow path of the delivery assembly 210 to prevent the fluid within the delivery assembly 210 from continuing to flow, thereby preventing the delivery assembly 210 from generating an unintended gravitational infusion of the fluid that may cause harm to the patient.

Figure 5:
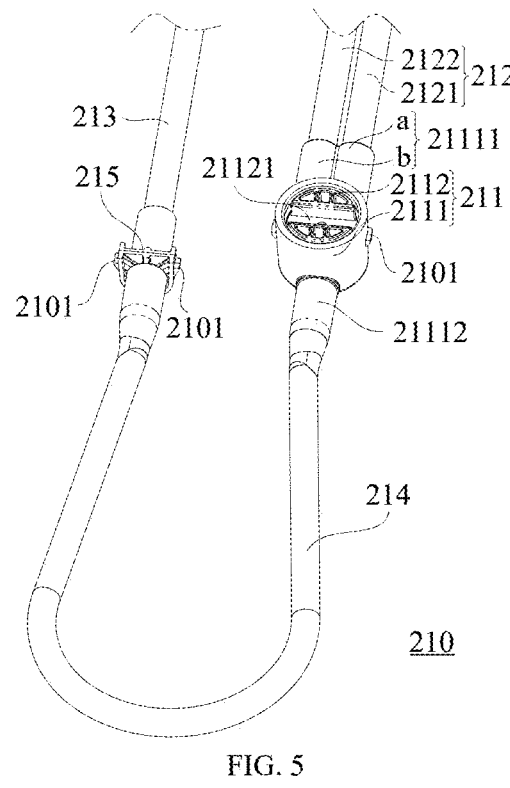
FIG. 5 shows a schematic structural diagram of a delivery assembly provided by embodiments of the invention.

FIG. 5 shows a schematic structural diagram of a delivery assembly provided by embodiments of the invention. As shown in FIG. 5, the delivery assembly 210 includes at least one inlet tube 212 and an outlet tube 213. An inlet of each inlet tube 212 is connected to a corresponding fluid storage device (e.g., a fluid storage bag or a fluid storage box), and an outlet of the fluid outlet tube 213 is connected to the patient's nasal cavity or oral cavity, for example, the fluid outlet tube 213 is connected to the patient's nasal cavity through a nasal tube, and a valve mechanism 211 is connected between the outlet of each inlet tube 212 and the inlet of the fluid outlet tube 213.

For the valve mechanism 211 provided in the flow path of the delivery assembly 210, the valve mechanism 211 may be connected between the respective inlet tube 212 and the fluid outlet tube 213. The valve mechanism 211 is provided with at least one inlet 21111 and an outlet 21112. Each inlet 21111 of the valve mechanism 211 is in communication with the respective inlet tube 212, and the outlet 21112 of the valve mechanism 211 is in communication with the fluid outlet tube 213. In other words, the outlet of each inlet tube 212 of the delivery assembly 210 is in communication with the corresponding inlet 21111 of the valve mechanism 211, and the inlet of the fluid outlet tube 213 of the delivery assembly 210 is in communication with the outlet 21112 of the valve mechanism 211.

As shown in FIG. 5, in this embodiment, the delivery assembly 210 may further include a connecting tube 214, which is connected between the valve mechanism 211 and the fluid outlet tube 213. One end of the connecting tube 214 is connected to the outlet 21112 of the valve mechanism 211, the other end of the connecting tube 214 is connected to the inlet of the fluid outlet tube 213 through the tube connector 215, and the fluid outlet tube 213 is in communication with the outlet of the valve mechanism 211 through the connecting tube 214. In other words, each of the fluid inlet tube 212, the connecting tube 214, and the fluid outlet tube 213 together form a flow path of the delivery assembly 210, and the valve mechanism 211 and the tube connector 215 are provided on the flow path.

By providing the connecting tube 214 between the valve mechanism 211 and the fluid outlet tube 213, the connecting tube 214 and the fluid outlet tube 213 are connected by the tube connector 215. In this way, the connecting tube 214 may be completely separated from the delivery assembly 210. When the fluid delivery mechanism 200 is assembled with the roller 300 mounted on the pump main body 100, the connecting tube 214 may be wound around the outer periphery of the roller 300 (as shown in FIG. 1), avoiding the fluid outlet tube 213 from being extruded by the roller 300. When the connecting tube 214 is extruded and deformed, only the connecting tube 214 needs to be replaced, and no other parts of the delivery assembly 210 need to be replaced, which can save the cost of the fluid delivery mechanism 200.

Moreover, for the delivery assembly 210 disposed around the periphery of the roller 300, the valve mechanism 211 and the tube connector 215 are disposed on both sides of the delivery assembly 210. The valve mechanism 211 and the tube connector 215 may be utilized to fix the delivery assembly 210 on the connecting base 220, so as to fix both sides of the delivery assembly 210, and to ensure that the delivery assembly 210 is stably and reliably fixed on the connecting base 220. The connecting base 220 has a better shaping effect on the delivery assembly 210, which can help the connecting tube 214 in the delivery assembly 210 to maintain a state similar to a "U-shaped" bend, so as to make it easy for the connecting tube 214 to be wound around the roller 300.

Of course, in other embodiments, the delivery assembly 210 may not be provided with the connecting tube 214, and the inlet of the fluid outlet tube 213 is directly connected to the outlet 21112 of the valve mechanism 211, and the fluid outlet tube 213 itself may be bent similar to a "U-shape", so that the fluid outlet tube 213 can be wound around the outer perimeter of the roller 300. In particular, a fixing structure is provided on the outer wall of the fluid outlet tube 213, and a fixing structure is provided on the valve mechanism 211 and the outer wall of the fluid outlet tube 213, so as to fix both sides of the delivery assembly 210 to the connecting base 220.

The following are all illustrated as an example that the delivery assembly 210 includes a connecting tube 214 connected between the valve mechanism 211 and the fluid outlet tube 213, and the connecting tube 214 is connected to the fluid outlet tube 213 through the tube connector 215.

When the connecting tube 214 of the delivery assembly 210 is disposed around the outside of the roller 300, the support base 150 mounted on the pump main body 100 may be configured to guide and limit the connecting tube 214, two accommodation grooves 151 may be provided on the support base 150, and the connecting tubes 214 disposed on the two sides of the roller 300 are extended into each of the two accommodation grooves 151 (as shown in FIG. 1).

Moreover, some sensors may be arranged in the parts of the accommodation grooves 151 to detect the operating state of the delivery assembly 210. For example, the accommodation grooves 151 may be provided with a bubble sensor 1511 and a pressure sensor 1512. The bubble sensor 1511 is configured to detect bubbles in the connecting tube 214 to determine whether there is any interruption of the flow of the fluid in the delivery assembly 210 or whether there is any problem of the flow of the fluid in the delivery assembly 210, such as flow interruption or flow too slow. The pressure sensor 1512 is configured to detect the pressure within the connecting tube 214 to determine whether the flow and flow rate of the fluid within the delivery assembly 210 is normal. The bubble sensor 1511 and the pressure sensor 1512 may be separately provided in the two accommodation grooves 151 to ensure that both the pressure sensor 1512 and the bubble sensor 1511 have sufficient installation space.

As for the specific structure of the valve mechanism 211, as shown in FIG. 5, the valve mechanism 211 includes a valve housing 2111 and a valve core 2112. The valve housing 2111 is provided with a cavity, the valve core 2112 is mounted within the cavity of the valve housing 2111, and the valve core 2112 is rotatable within the valve housing 2111. Each inlet 21111 and outlet 21112 of the valve mechanism 211 is provided on the valve housing 2111. In other words, the valve housing 2111 is provided with at least one inlet 21111 and outlet 21112, and each inlet 21111 and outlet 21112 on the valve housing 2111 is in communication with the cavity within the valve housing 2111.

Under control of the pump main body 100, the valve core 2112 is rotatable between at least two positions, and the at least two positions include at least one open position and a closed position.

When the valve core 2112 is in an open position, the valve core 2112 is in communication with an inlet 21111 of the valve housing 2111 and an outlet 21112. In other words, when the valve core 2112 is in the open position, the valve core 2112 permits fluid to flow from the one inlet 21111 of the valve housing 2111 to the outlet 21112. When the valve core 2112 is in the closed position, the valve core 2112 is not connectable with any inlet 21111 of the valve housing 2111 to the outlet 21112. In other words, when the valve core 2112 is in the closed position, the valve core 2112 prevents fluid from flowing from any inlet 21111 of the valve housing 2111 to the outlet 21112.

After the fluid delivery mechanism 200 is assembled to the pump main body 100, the pump main body 100 may control the motion state of the valve core 2112 of the valve mechanism 211 in response to commands entered by an operator. When the valve core 2112 is in the open position, a certain inlet 21111 of the valve mechanism 211 is in communication with the outlet 21112, and the valve mechanism 211 may be in communication with the corresponding inlet tube 212 and the fluid outlet tube 213. The fluid in the fluid storage device connected to the inlet of the fluid inlet tube 212 may enter the fluid inlet tube 212 and flow from the fluid inlet tube 212 to the fluid outlet tube 213, and finally be delivered by the fluid outlet tube 213 to the patient. When the valve core 2112 is in the closed position, any inlet 21111 of the valve mechanism 211 is not in communication with the outlet 21112, and the valve mechanism 211 blocks all the connecting paths between the fluid inlet tube 212 and the fluid outlet tube 213, and the fluid in the storage device connected to the inlets of all the fluid inlet tubes 212 cannot enter the fluid outlet tube 213, so as to prevent free-flow phenomenon of the fluid within the delivery assembly 210.

As shown in FIG. 5, it is shown that the delivery assembly 210 includes two inlet tubes 212, which may be used to deliver different fluids. In other words, the fluids carried within the fluid storage devices connected to the inlets of the two inlet tubes 212 may be different. For ease of illustration, the two inlet tubes 212 of the delivery assembly 210 are defined as a first fluid inlet tube 2121 and a second fluid inlet tube 2122 in this embodiment. As an example, the fluid delivered by the first fluid inlet tube 2121 is a nutrient fluid, and the fluid delivered by the second fluid inlet tube 2122 is a cleaning fluid (e.g., saline or purified water).

Correspondingly, two inlets 21111 are provided on the valve housing 2111 of the valve mechanism 211. For ease of illustration, the two inlets 21111 on the valve housing 2111 are defined as a first inlet 21111a and a second inlet 21111b. The first fluid inlet tube 2121 of the delivery assembly 210 is connected to the first inlet 21111a on the valve housing 2111, and the second fluid inlet tube 2122 of the delivery assembly 210 is connected to the second inlet 21111b on the valve housing 2111.

In this way, the valve core 2112 may have two open positions, which are a first open position and a second open position. When the valve core 2112 is in the first open position, the first fluid inlet tube 2121 is in communication with the fluid outlet tube 213, and the nutrient solution in the first fluid inlet tube 2121 may flow to the fluid outlet tube 213 to deliver the nutrient solution to the patient. When the valve core 2112 is in the second open position, the second fluid inlet tube 2122 is in communication with the fluid outlet tube 213, and the cleaning solution in the second fluid inlet tube 2122 may flow to the fluid outlet tube 213 to clean the piping of the delivery assembly 210.

In addition to the delivery assembly 210 including two fluid inlet tubes 212 shown in the figures, in other embodiments, the delivery assembly 210 may also include only one inlet tube 212, which may be configured to deliver nutrient fluid or cleaning fluid. In this circumstance, the valve core 2112 may have an open position, and when the valve core 2112 is in the open position, the fluid inlet tube 212 is in communication with the fluid outlet tube 213.

Of course, the delivery assembly 210 may also include more than three fluid inlet tubes 212, and the different inlet tubes 212 are configured to deliver different fluids, so that the delivery assembly 210 includes three inlet tubes 212. For example, the three inlet tubes 212 may be configured to deliver a first nutrient solution, a second nutrient solution, and a cleaning solution, respectively. In this circumstance, the valve core 2112 may also have more than three open positions. In different open positions, the corresponding inlet tubes 212 are in communication with the fluid outlet tube 213, and the fluid in the corresponding inlet tubes 212 may flow to the fluid outlet tube 213.

Figure 6:
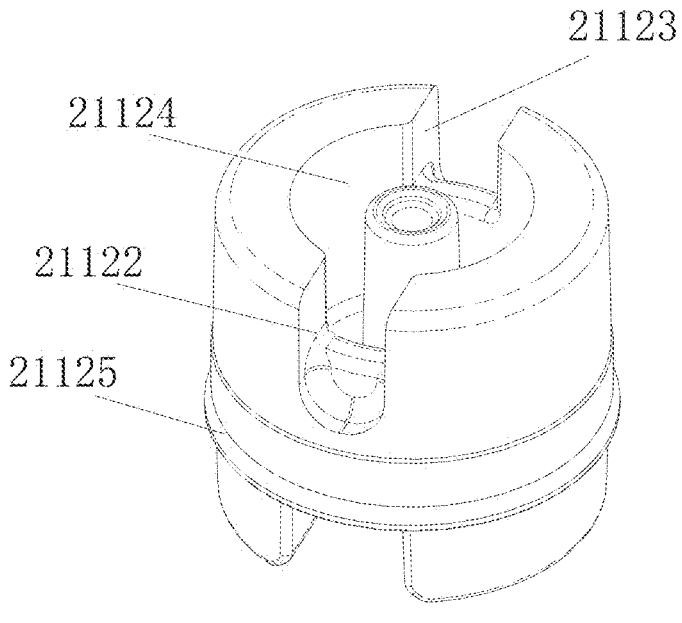
FIG. 6 shows a schematic structural diagram of a valve core provided by embodiments of the invention.
Figure 7:
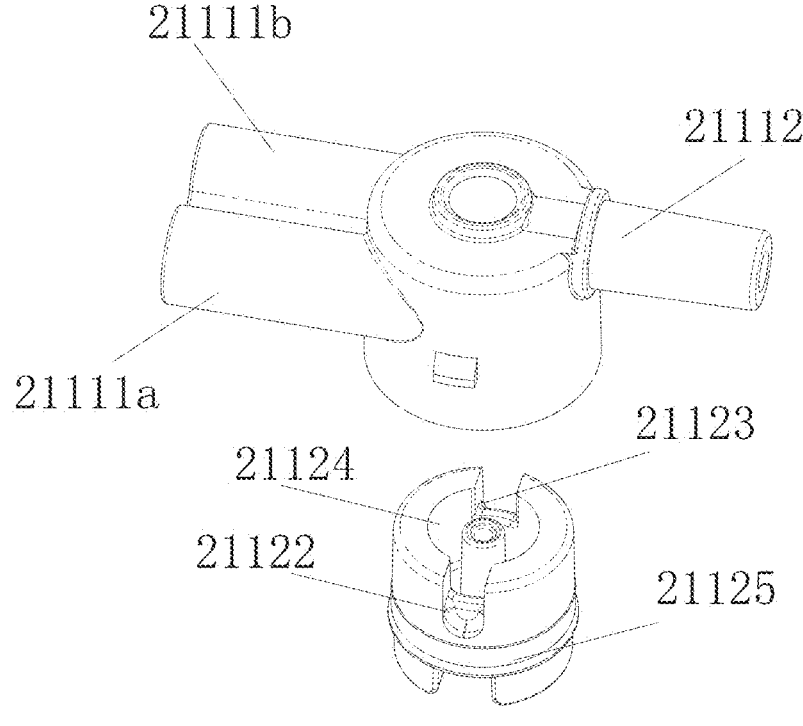
FIG. 7 shows an exploded view of the valve core and the valve housing in one view provided by the embodiment of the invention.

In some embodiments, as shown in FIGS. 6-7, a first opening 21122 and a second opening 21123 are provided on the circumference of the valve core 2112, and the valve core 2112 defines a fluid passage 21124 with the valve housing 2111. The fluid passage 21124 is in communication with the first opening 21122, the second opening 21123, and the outlet 21112 of the valve housing.

Specifically, as shown in FIG. 6, the valve core 2112 has an overall cylindrical structure, and the first opening 21122 and the second opening 21123 are notched structures of the valve core 2112 opened from the same end face in an axial direction on a circumferential surface. As an example, the first opening 21122 and the second opening 21123 may be presented as a U-shaped notched structure.

Figure 8:
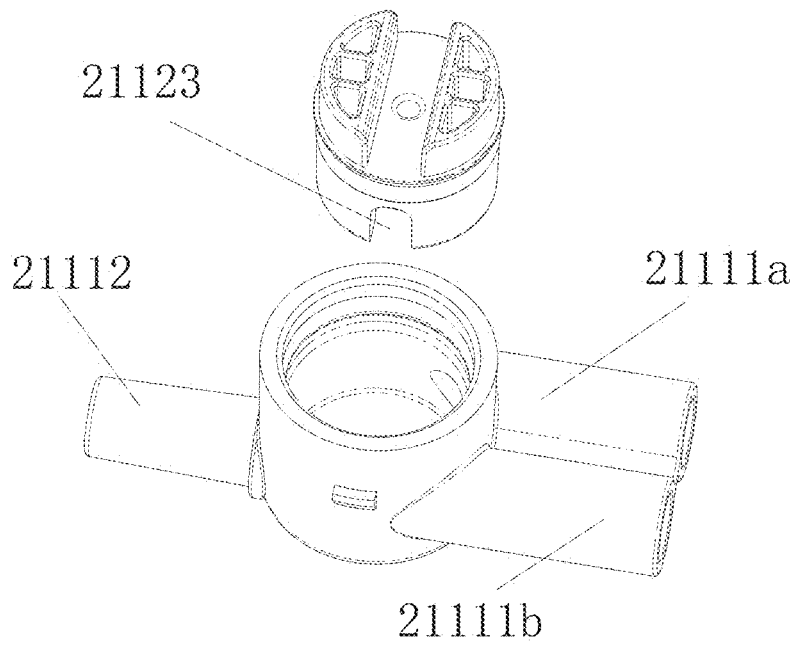
FIG. 8 shows an exploded view of the valve core and the valve housing in another view provided by the embodiment of the invention.

In some embodiments, as shown in FIGS. 7-8, one end of the valve housing 2111 is recessed inwardly to form a first recess groove 21113 that accommodates the valve core 2112, and a depth of the first recess groove 21113 is greater than a height of the valve core 2112. The outlet 21112 of the valve housing 2111 is provided on a side wall close to a bottom surface of the first recess groove 21113. When the valve core 2112 is fitted into the first recess groove 21113 of the valve housing through the opening of the first recess groove 21113, a limit structure 21125 of the valve core 2112 is configured to suspend and fit the valve core 2112 in the first recess groove 21113 of the valve housing. The fluid passage 21124 is formed between an end surface of the valve core 2112 facing the bottom of the first recess groove 21113 and a bottom surface of the first recess groove 21113. Further, an end of the valve core 2112 toward the bottom of the first recess groove 21113 is recessed inwardly along a height direction to form a second recess groove. The space enclosed by the second recess groove may also serve as a portion of the fluid passage 21124, thereby increasing the volume of the fluid passage 21124. Moreover, the peripheral surface of the valve core 2112 cannot block the outlet 21112 of the valve housing, and the outlet 21112 is always in communication with the interior of the valve housing when the valve core 2112 is rotated inside the valve housing 2111. In other words, the fluid passage 21124 and the outlet 21112 are always in communication.

Figures 9, 10:
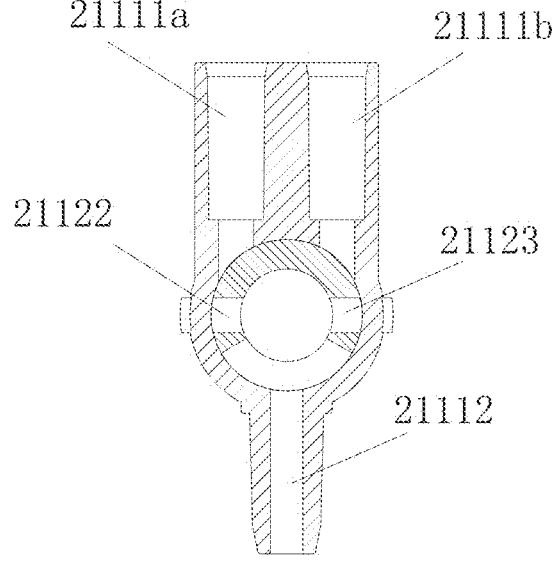
FIG. 9 is a schematic diagram of the valve core in a cut-off state provided by embodiments of the invention.
FIG. 10 is a schematic diagram of the valve core in a conduction state provided by embodiments of the invention.

As shown in FIG. 9, when the valve core 2112 is in an initial position, the first opening 21122 and the second opening 21123 are located on each side of the inlet 21111 of the valve housing. In this circumstance, the peripheral surface of the valve core cuts off the inlet 21111 from the fluid passage 21124, and the delivery assembly 210 is in a cutoff state. In one embodiment, there is only one number of inlets 21111 in the valve housing. In this circumstance, the fluid delivery mechanism is configured to deliver only one type of nutrient fluid. When the pump main body 100 controls the nutrient fluid for delivery, the valve core 2112 may be rotated in a first direction to make one of the first opening 21122 and the second opening 21123 in communication with the inlet 21111. As an example, the pump main body may control the valve core to rotate so that the first opening 21122 is in communication with the inlet 21111, and the first direction is clockwise. Alternatively, the pump main body 100 may control the valve core 2112 to rotate so that the second opening 21122 is in communication with the inlet 21111, and the first direction is counterclockwise. In this embodiment, only one of the openings of the control valve core is required to be in communication with the inlet 21111, and the user can set it according to the practical needs, which is not limited herein.

In some embodiments, the inlet 21111 of the valve housing 2111 includes a first inlet 21111*a* and a second inlet 21111*b*, and the first inlet 21111*a* and the second inlet 21111*b* are disposed side by side of the valve housing 2111. As shown in FIG. 9, when the valve core 2112 is in an initial position, the first opening 21122 is provided on a side of the first inlet 21111*a* away from the second inlet 21111*b*, and the second opening 21123 is provided on a side of the second inlet 21111*b* away from the first inlet 21111*a*.

As shown in FIG. 10, when the pump main body 100 controls the valve core 2112 to be rotated in the first direction from the initial position to the first position, the first opening 21122 is in communication with the first inlet 21111*a*, so that the fluid from the first inlet 21111*a* can pass through the first opening 21122, the fluid passage 21124, and flow out from the outlet 21112 of the valve housing 2111 in turn, and the delivery assembly is in a conduction state.

Figure 11:
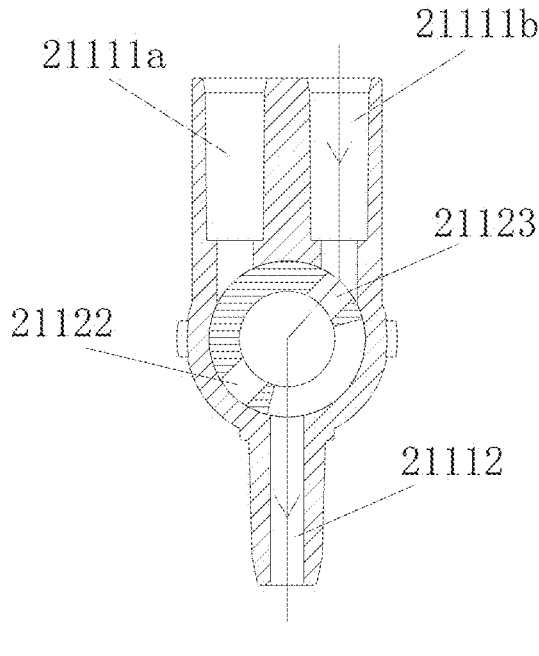
FIG. 11 is a schematic diagram of the valve core in another conduction state provided by embodiments of the invention.

As shown in FIG. 11, when the pump main body 100 controls the valve core 2112 to be rotated from the initial position to the second position in the second direction, the second opening 21123 is in communication with the second inlet 21111*b*, so that the fluid from the second inlet 21111*b* can pass through the second opening 21122, the fluid passage 21124 in turn, and flow out of the outlet 21112 of the valve housing 2111, and the delivery assembly is in a conduction state. The first direction and the second direction are opposite, for example, the first direction may be clockwise, and the second direction is counterclockwise. It is to be noted that FIGS. 9-11 are only used to illustrate a schematic diagram of the state in which the valve core is in the conduction or cut-off state, and are not intended to limit the specific structure of the valve core 2112 and the valve housing 2111.

In the prior art, the fluid delivery mechanism of a nutrient pump is usually provided with only one opening in the fluid delivery mechanism to correspond to the inlets of the two fluid delivery passages, realizing the conduction of the two fluids. However, in such a nutrient pump, either the opening is needed to conduct two inlets separately in different directions, and this solution requires a larger rotational angle of the opening, and the switching efficiency is lower. Either the openings are required to guide two inlets in the same direction, but in the case of guiding the more distant inlet must pass through the closer inlet, which will lead the liquid in the closer inlet into the opening, resulting in the phenomenon of mixing liquid. In the embodiment of this invention, the two openings provided on the valve core correspond to the two inlets on the valve housing, and the first opening 21122 is made to be in communication with the first inlet 21111*a* or the second opening 21123 is made to be in communication with the second inlet 21111*b* by different rotational directions, so as to switch the conduction cut-off state of the delivery assembly more efficiently. Moreover, the conduction of the two inlets is independent of each other and does not affect each other, thereby avoiding mixing of the liquids in the two inlets in the conduction state of the delivery assembly 210.

In some embodiments, the first opening 21122 and the second opening 21123 are symmetrically provided along a radial direction of the valve core 2112. The first inlet 21111*a* and the second inlet 21111*b* are provided side by side on the valve housing 2111. When the valve core 2112 is in an initial position, a centerline between the first inlet 21111*a* and the second inlet 21111*b* is perpendicular to a line joining the first opening 21122 and second opening 21123. When the valve core 2112 is rotated at an angle H in the initial position in a first direction (e.g., clockwise), the first inlet 21111*a* is in communication with the first opening 21122. In this circumstance, the fluid in the first inlet 21111*a* can pass through the first opening 21122 and the fluid passage 21124 of the valve core in turn, and then flow out the outlet 21112. When the valve core 2112 is rotated at an angle Hin a second direction (e.g., counterclockwise) from the initial position, the second inlet 21111*b* is in communication with the second opening 21123. In this circumstance, the liquid in the second inlet 21111*b* can pass through the second opening 21123 and the fluid passage 21124 of the valve core, and then flow out of the outlet 21112. The rotational angle H for realizing the conduction of the valve core may be 0-90°, and the rotational angle H is adjusted according to the spacing between the first inlet 21111*a* and the second inlet 21111*b*. In one embodiment, the rotational angle may be 60°.

In addition, when the delivery assembly 210 is mounted on the pump main body 100, the delivery assembly 210 is substantially "U-shaped" so that the fluid inlet tube 212 and the connecting tube 214 located on the same side of the delivery assembly 210 are arranged in a substantially straight line. In this way, the inlet 21111 and the outlet 21112 of the valve housing 2111 of the valve mechanism 211 may be provided opposite to each other. As an example, the delivery assembly 210 includes the first fluid inlet tube 2121 and the second fluid inlet tube 2122 that may be disposed side by side. Correspondingly, the first inlet 21111*a* and the second inlet 21111*b* on the valve housing 2111 may be disposed side by side on opposite sides of the outlet 21112.

As for the specific manner in which the pump main body 100 drives the valve core 2112 of the valve mechanism 211 to rotate, as shown in FIG. 5, the end of the valve housing 2111 facing the pump main body 100 may be open, the opening of the valve core 2112 may be mounted in a cavity of the valve housing 2111, a reversing groove 21121 may be provided on a side of the valve core 2112 facing the pump main body 100, and the reversing groove 21121 exposed within the opening of the valve housing 2111. As shown in FIG. 2, the pump main body 100 is provided with a switching member 160, and the switching member 160 extends into the reversing groove 21121 of the valve core 2112 and drives the valve core 2112 to move to realize the switching of the valve core 2112 between different positions.

It should be noted that the pump main body 100 is also provided with a driving mechanism to drive the switching member 160 to move. After the pump main body 100 receives an instruction inputted by an operator, the pump main body 100 drives the switching member 160 via the driving mechanism to move the switching member 160, so that the switching member 160 drives the reversing groove 21121 to move to a corresponding range, so as to cause the valve core 2112 to be switched to a corresponding position, for example, to cause the valve core 2112 to be switched from a closed position to a certain open position, or, to cause the valve core 2112 to be switched from a certain open position to another open position, or, to cause the valve core 2112 to be switched from a certain open position to a closed position.

In the embodiment shown in the figures, the switching member 160 is a rotating shaft structure, and the driving mechanism drives the switching member 160 to realize the switching of the valve core 2112 between different positions. It should be understood that in other embodiments, the driving mechanism may also drive the switching member 160 to translate or make other movements to realize the switching of the valve core 2112 between different positions.

In addition, the shape and size of the switching member 160 on the pump main body 100 should match the shape and size of the reversing groove 21121 on the valve core 2112, so that the switching member 160 can extend into the reversing groove 21121 on the valve core 2112 and the switching member 160 can be realized to drive the valve core 2112 to move.

As an example, the reversing groove 21121 on the valve core 2112 may be a through groove passing through opposite sides of the valve core 2112, or the reversing groove 21121 on the valve core 2112 may be a non-through groove, and the shapes of the reversing groove 21121 may be square, triangular, parallelogram, trapezoid, and the like.

Typically, before the fluid delivery mechanism 200 is assembled to the pump main body 100, the valve core 2112 of the valve mechanism 211 should be in the closed position to block all the flow paths within the delivery assembly 210, preventing free-flow phenomenon of the fluid within the delivery assembly 210. In this circumstance, the orientation of the switching member 160 on the pump main body 100 should correspond to the orientation of the reversing groove 21121 on the valve core 2112, so that when the fluid delivery mechanism 200 is assembled to the pump main body 100, the switching member 160 can smoothly extend into the reversing groove 21121 of the valve core 2112.

When the fluid delivery mechanism 200 is assembled to the pump main body 100, the reversing groove 21121 on the valve core 2112 of the valve mechanism 211 is facing the pump main body 100, and it is not easy to observe the orientation of the reversing groove 21121. In order to enable the fluid delivery mechanism 200 to be smoothly assembled to the pump main body 100, this embodiment locates the initial position of the valve core 2112, or in other words, locates the initial position of the valve core 2112 when it is in the closed position, so that the switching member 160 can be smoothly extended into the reversing groove 21121. In other words, the orientation of the reversing groove 21121 when the valve core 2112 is in the closed position is limited to ensure that the reversing groove 21121 on the valve core 2112 can be aligned with the switching member 160 on the pump main body 100.

For example, if the reversing groove 21121 on the valve core 2112 is a through groove passing through opposite sides of the valve core 2112, when the valve core 2112 of the valve mechanism 211 is in the closed position, the reversing groove 21121 may be positioned transversely between the inlet 21111 and the outlet 21112 of the valve housing 2111. For example, the extension direction of the reversing groove 21121 may be perpendicular to the outlet 21112 of the valve housing 2111, and the extension direction of the reversing groove 21121 may be perpendicular to the outlet 21112 of the valve housing 2111. In this way, when assembling the valve mechanism 211, the mounting orientation of the valve core 2112 may be adjusted according to the position of the outlet 21112 on the valve housing 2111 so that the reversing groove 21121 of the valve core 2112 is perpendicular to the outlet 21112 of the valve housing 2111, in order to accurately position the initial position of the valve core 2112.

Figure 12:
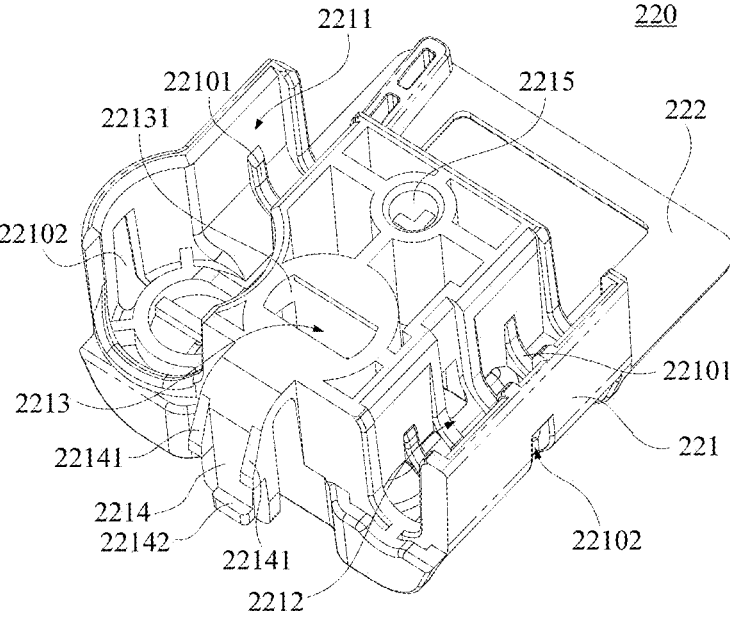
FIG. 12 is a schematic structural diagram of a connecting base provided by embodiments of the invention.

FIG. 12 is a schematic structural diagram of a connecting base provided by embodiments of the invention. As shown in FIG. 4 and FIG. 12, as for the specific structure of the connecting base 220, the connecting base 220 may include a main body portion 221, and the delivery assembly 210 may be mounted on the main body portion 221 of the connecting base 220, relying on the main body portion 221 of the connecting base 220 to secure the delivery assembly 210.

The main body portion 221 of the connecting base 220 may be provided mainly corresponding to the portions where the valve mechanism 211 and the tube connector 215 of the delivery assembly 210 are located. Both the valve mechanism 211 and the tube connector 215 may be connected to the main body portion 221 to fix the delivery assembly 210 on the main body portion 221. The bent portion of the connecting tube 214 may be located outside of the connecting base 220 to avoid interference between the connecting base 220 and the roller 300 when the fluid delivery mechanism 200 is mounted to the pump main body 100, thereby ensuring that the connecting tube 214 is set on the roller 300 smoothly.

On the basis of ensuring that the connecting base 220 does not interfere with the roller 300 and does not affect the connection between the connecting tube 214 and the roller 300, the connecting base 220 may also include a pressing plate 222 attached to the main body portion 221. The pressing plate 222 may be integrally molded on the main body portion 221, and the pressing plate 222 may be disposed at an end of the main body portion 221 toward the connecting tube 214, and the pressing plate 222 may be disposed at an end of the main body portion 221 back away from the pump main body 100. For example, the pressing plate 222 may extend from the side of the main body portion 221 back away from the pump main body 100 (as shown in FIG. 1).

The pressing plate 222 of the connecting base 220 is blocked above the support base 150 on the pump main body 100. Under the joint action of the pressing plate 222 and the support base 150, the connecting tube 214 is confined within the accommodation groove 151 of the support base 150 to ensure stable contact between the connecting tube 214 and sensors (e.g., the air bubble sensor 1511 and the pressure sensor 1512) within the accommodation groove 151, thereby ensuring the detection effect of the sensors.

In addition, in the process of the roller 300 rotating and squeezing the connecting tube 214, the connecting tube 214 will inevitably produce a small amplitude of shaking, by setting the pressing plate 222 on the connecting base 220 above the connecting tube 214, the pressing plate 222 has a resisting effect on the shaking of the connecting tube 214, so as to reduce the amplitude of the shaking of the connecting tube 214, and improve the stability of the connecting tube 214.

As shown in FIG. 12, as for the fixing method of the delivery assembly 210 on the connecting base 220, in this embodiment, the connecting base 220 may also be provided with a first locking structure, the first locking mechanism may be located in the main body 221 of the connecting base 220, and the valve mechanism 211 may be detachably connected to the first locking mechanism to fix the valve mechanism 211 on the connecting base 220.

The first locking mechanism may be a first limit groove 2211 provided in the connecting base 220, and a groove opening of the first limit groove 2211 may be oriented toward the pump main body 100. In other words, the first limit groove 2211 extends from one side of the connecting base 220 toward the pump main body 100 to the other side of the connecting base 220, and the valve mechanism 211 of the delivery assembly 210 is mounted in the first limit groove 2211. In this way, the reversing groove 21121 on the valve core 2112 of the valve mechanism 211 is exposed to the groove of the first limit groove 2211 so as to facilitate the connection of the reversing groove 21121 of the valve core 2112 to the switching member 160 on the pump main body 100. Besides, the bottom of the groove of the first limit groove 2211 is sheltered above the valve mechanism 211, forming a protection of the valve mechanism 211 in case the valve mechanism 211 is externally damaged.

As shown in FIGS. 4 and 12, the space occupied by the main body portion 221 of the connecting base 220 may be large, and the main body portion 221 is not limited to being cooperatively connected to the valve mechanism 211. The extension length of the first limit groove 2211 on the main body portion 221 that serves as the first locking mechanism may also be long. The first limit groove 2211 may include at least two portions, one portion corresponding to the valve mechanism 211, the contour of which may match the outer contour of the valve mechanism 211, and the other portion may correspond to a connection part of the connecting tube 214 and the valve mechanism 211. The connection portion of the valve mechanism 211 and the connecting tube 214 may be supported within the first limit groove 2211, and an inner side wall of the first limit groove 2211 may be provided with raised limit strips 22101. The connecting parts of the valve mechanism 211 and the connecting tube 214 are snap-fitted between the limit strips 22101 on both sides.

The first limit groove 2211 and the valve mechanism 211 are provided with an interlocked positioning structure to lock the valve mechanism 211 within the first limit groove 2211. For example, the first limit groove 2211 is provided with snap slots 22102 (as shown in FIG. 12) on both sides of the slot wall corresponding to the portion of the valve mechanism 211. The valve housing 2111 of the valve mechanism 211 is provided with snap fasteners 2101 (as shown in FIG. 5) on both sides of the outer side wall of the valve mechanism 211, and the snap fasteners 2101 of the valve mechanism 211 are snapped into the snap slots 22102 of the first limit groove 2211 to lock the valve mechanism 211 in the first limit groove 2211 (as shown in FIG. 4).

In addition, it will be appreciated that when the snap fasteners 2101 are provided on both sides of the outer sidewalls of the valve housing 2111 of the valve mechanism 211, for the case where the initial position of the valve core 2112 is such that the direction of extension of the reversing groove 21121 is perpendicular to the outlet 21112 of the valve housing 2111, it is also possible to locate the valve core 2112 in accordance with the snap fasteners 2101 on both sides of the valve housing 2111, so that both sides of the valve core 2112 of the ends of the reversing groove 21121 correspond to the snap fasteners 2101 on each side of the valve housing 2111 so that the valve core 2112 is in the orientation corresponding to its closed position.

As shown in FIG. 12, the connecting base 220 may also be provided with a second locking structure for fixing the tube connector 215 on the connecting base 220, and the second locking mechanism may be located in the main body portion 221 of the connecting base 220. The tube connector 215 may be detachably connected to the second locking mechanism to fix the tube connector 215 on the connecting base 220.

Similar to the first locking mechanism being a first limit groove 2211 provided on the main body portion 221, the second locking mechanism may be a second limit groove 2212 provided on the main body portion 221, and a groove opening of the second limit groove 2212 may also be oriented toward the pump main body 100. In other words, the second limit groove 2212 extends from the side of the connecting base 220 oriented toward the pump main body 100 toward the other side of the connecting base 220. The tube connector 215 of the delivery assembly 210 is mounted within the second limit groove 2212. In this way, the bottom of the second limit groove 2212 is shielded over the tube connector 215, forming a protection for the tube connector 215 against destruction of the tube connector 215 by an external force.

Moreover, the extension length of the second limit groove 2212 as the second locking mechanism on the main body portion 221 may also be longer, the tube connector 215 may be installed in the middle portion of the second limit groove 2212. The connection portion between the tube connector 215 and the connecting pipe 214, and the connection portion between the tube connector 215 and the fluid outlet tube 213 are located at opposite ends of the second limit groove 2212, respectively. The inner sidewall of the second limit groove 2212 may also be provided with raised limit strips 22101. The connection portion between the tube connector 215 and the connecting tube 214, and the connection portion between the tube connector 215 and the fluid outlet tube 213 are all snapped between the limit strips 22101 on both sides.

The second limit groove 2212 and the tube connector 215 are also provided with an interlocked positioning structure to lock the tube connector 215 within the second limit groove 2212. Similar to the mating of the first limit groove 2211 and the valve mechanism 211, the groove walls of both sides of the second limit groove 2212 corresponding to the portion of the tube connector 215 are provided with snap slots 22102 (as shown in FIG. 12), and the outer walls of both sides of the tube connector 215 are provided with snap fasteners 2101 (as shown in FIG. 5). The snap fasteners 2101 of the tube connector 215 are snapped into the snap slots 22102 of the second limit groove 2212, to snap the tube connector 215 into the second limit groove 2212 (as shown in FIG. 4).

As an example, the first limit groove 2211 and the second limit groove 2212 provided on the main body portion 221 of the connecting base 220 are located on both sides of the main body portion 221, and the dimensions of the connecting base 220 may be matched with the dimensions of the delivery assembly 210 to rationalize the design of the connecting base 220. Moreover, a part on the connecting base 220 located between the first limit groove 2211 and the second limit groove 2212 may also be designed to utilize the part to realize the connection between the connecting base 220 and the pump main body 100, so as to fully utilize the space of the connecting base 220.

Of course, in other examples, the first locking structure and the second locking structure on the connecting base 220 may also be other structures, and the valve mechanism 211 and the tube connector 215 of the delivery assembly 210 may also be connected to the connecting base 220 in other ways. For example, the first locking structure and the second locking structure on the connecting base 220 may be locking holes provided on the main body 221, and corresponding mounting holes are provided on the valve mechanism 211 and the pipe connector 215 of the delivery assembly 210. The delivery assembly 210 is fixed to the connecting base 220 by threading screws, bolts, and other fasteners into the locking holes and the mounting holes.

Both of the following are illustrated by taking the first locking structure and the second locking structure on the connecting base 220 as examples of the first limit groove 2211 and the second limit groove 2212 provided on both sides of the main body portion 221 thereof, respectively.

As for the connection method between the connecting base 220 and the pump main body 100, as shown in FIG. 12, the connecting base 220 is also provided with a first positioning structure, and the first positioning structure is configured to cooperate with the anti-disconnecting member 170 (as shown in FIG. 2) provided on the pump main body 100. The pump main body 100 is provided with a driving mechanism for driving the movement of the anti-disconnecting member 170, to lock the connecting base 220 with the pump main body 100. Alternatively, the connecting base 220 may also be separated from the pump main body 100.

In an embodiment, the anti-disconnecting member 170 has a locked position or an unlocked position. When the anti-disconnecting member 170 is in the locked position, the connecting base 220 is locked to the pump main body 100. When the anti-disconnecting member 170 is in the unlocked position, the connecting base 220 is separated from the pump main body 100. In the embodiment shown in the figures, the anti-disconnecting member 170 is a rotating shaft structure, and the driving mechanism drives the anti-disconnecting member 170 to rotate the anti-disconnecting member 170 to switch the anti-disconnecting member 170 to the locked position or the unlocked position. It will be appreciated that in other embodiments, the driving mechanism may also drive the anti-disconnecting member 170 to translate or other movements to switch the anti-disconnecting member 170 to the locked position or the unlocked position.

As an example, one driving mechanism may be provided within the pump main body 100 to drive both the switching member 160 and the anti-disconnecting member 170 to move. Alternatively, the pump main body 100 is provided with two driving mechanisms for driving the switching member 160 and the anti-disconnecting member 170 to move, respectively, which is not limited in this embodiment.

In an embodiment, the second positioning structure may be an anti-disconnecting hole 22131 provided on the connecting base 220, and the anti-disconnecting member 170 on the pump main body 100 may pass through the anti-disconnecting hole 22131 on the connecting base 220. The anti-disconnecting member 170 may be rotated to a locked position or an unlocked position under the driving action of the pump main body 100. When the anti-disconnecting member 170 is in the locked position, the anti-disconnecting member 170 stops at the outer periphery of the anti-disconnecting hole 22131 to lock the connecting base 220 to the pump main body 100. When the anti-disconnecting member 170 is in the unlocked position, the anti-disconnecting member 170 is located within the opening of the anti-disconnecting hole 22131, and the connecting base 220 is disengaged from the anti-disconnecting member 170 to detach the fluid delivery mechanism 200 from the pump main body 100.

As shown in FIGS. 3 and 12, the connecting base 220 may be provided with a positioning groove 2213, which may be disposed between the first limit groove 2211 and the second limit groove 2212. The groove opening of the positioning groove 2213 may be disposed on a side of the connecting base 220 back away from the pump main body 100. In other words, the positioning groove 2213 may be disposed from the side of the connecting base 220 back away from the pump main body 100 toward the other side of the connecting base 220. The anti-disconnecting hole 22131 may be disposed at the bottom of the positioning groove 2213, and a portion of the bottom of the positioning groove 2213 disposed on both sides of the anti-disconnecting hole 22131 forms a stop surface of the anti-disconnecting member 170. When the anti-disconnecting member 170 rotates and stops on the stop surface of the positioning groove 2213, the anti-disconnecting member 170 is in a locked position.

The anti-disconnecting member 170 on the pump main body 100 may include a main rod 171 and a locking rod 172 (as shown in FIG. 2). The main rod 171 may be connected to a driving mechanism within the pump main body 100, and the locking rod 172 is connected to the main rod 171. For example, the locking rod 172 is integrally formed in a top end of the main rod 171 and the locking rod 172 protrudes out to a side of the main rod 171. In this way, when the anti-disconnecting member 170 is rotated, the locking rod 172 may be rotated until it stops at the circumference of the anti-disconnecting hole 22131 to put the anti-disconnecting member 170 in the locked position. The locking rod 172 may be rotated until it is located entirely within the opening of the anti-disconnecting hole 22131 to put the anti-disconnecting member 170 in the unlocked position.

In some examples, a central portion of the locking rod 172 may be attached to the main rod 171, and the ends of the locking rod 172 extend to both sides of the main rod 171, such that when the anti-disconnecting member 170 is rotated to the locked position, the ends of the locking rod 172 are stopped on both sides of the anti-disconnecting hole 22131, respectively. The locking rod 172 may extend in a direction parallel to the plane in which the anti-disconnecting hole 22131 is located. Alternatively, there may be an angle between the locking rods 172 and the plane in which the anti-disconnecting hole 22131 is located. For example, the anti-disconnecting member 170 as a whole may have a "T-shaped" structure, and the locking rod 172 of the anti-disconnecting member 170 may have a "V-shaped" structure, an "inverted V-shaped" structure, "trapezoidal" structure, or 'inverted trapezoidal' structure, and the like.

In other examples, one end of the locking rod 172 may be attached to the main rod 171, and the locking rod 172 extends out of the side of the main rod 171, such that the locking rod 172 stops on the side of the anti-disconnecting hole 22131 when the anti-disconnecting member 170 is rotated to the locked position. Similarly, the locking rod 172 may extend in a direction parallel to the plane in which the anti-disconnecting hole 22131 is located. Alternatively, there may be an angle between the locking rod 172 and the plane in which the anti-disconnecting hole 22131 is located. For example, the anti-disconnecting member 170 may have an overall "inverted L-shaped" structure.

As shown in FIG. 12, in order to make the fluid delivery mechanism 200 more stable and securely mounted on the pump main body 100, in this embodiment, the connecting base 220 may also be provided with a second positioning structure, and a fixing structure (as shown in FIG. 2) may be provided in the accessory mounting area on the operation surface of the pump main body 100, and the second positioning structure of the connecting base 220 is detachably connected to the fixing structure of the pump main body 100, so as to connect the connecting base 220 to the fixing structure of the pump main body 100.

As an embodiment, the second positioning structure on the connecting base 220 may be a resilient snap 2214 (as shown in FIG. 3 or FIG. 12), and the resilient snap 2214 may protrude from a side wall of the main body portion 221 of the connecting base 220. Correspondingly, the fixing structure on the pump main body 100 may be a snap base 180 (as shown in FIG. 2), and the snap base 180 may be erected on the accessory mounting area in the operating surface of the pump main body 100. In this embodiment, the resilient snap 2214 is provided with at least one tab 22141, and the snap base 180 is provided with at least one slot 181 on a side facing the resilient snap 2214. The tab 22141 of the resilient snap 2214 is snapped into the slot 181 of the snap base 180 to snap-fit the connecting base 220 to the pump main body 100 (as shown in FIG. 1).

As an embodiment, one end of the resilient snap 2214 connected to the connecting base 220 may be proximate to the pump main body 100, with the other end of the resilient snap 2214 protruding in a direction away from the pump main body 100 so as to facilitate the snap of the resilient snap 2214 into the snap base 180 on the pump main body 100. Moreover, there is a certain gap between the resilient snap 2214 and the main body portion 221 of the connecting base 220 to reserve sufficient deformation space for the resilient snap 2214. After the resilient snap 2214 is snapped onto the snap base 180, the snap base 180 exerts pressure on the resilient snap 2214 in the direction towards the main body portion 221, and the resilient snap 2214 exerts an elastic force in the opposite direction and against the pressure, so the elastic force ensures that the resilient snap 2214 is reliably connected to the snap base 180.

On this basis, as shown in FIG. 3 or FIG. 12, the resilient snap 2214 is further provided with a stop portion 22142, which may be disposed at an end of the resilient snap 2214 away from the pump main body 100. The stop portion 22142 projects towards the snap base 180 on the pump main body 100, and the stop portion 22142 is able to stop on the top of the snap base 180 (as shown in FIG. 1). This facilitates operation by an operator, who can separate the resilient snap 2214 from the snap base 180 by pressing against the stop portion 22142 of the resilient snap 2214 in order to remove the fluid delivery mechanism 200 from the pump main body 100.

The resilient snap 2214 may be attached to a side of the connecting base 220 back away from the roller 300, and correspondingly, the snap base 180 on the pump main body 100 may be provided far away from the roller 300 to reserve sufficient setting space for the snap base 180. The roller 300 and the snap base 180 may be located on the two sides of the accessory mounting area on the operating surface of the pump main body 100, respectively. The switching member 160 and the anti-disconnecting member 170 may be set close to the snap base 180, and the support base 150 may be set between the roller 300 and the switching member 160 and the anti-disconnecting member 170, so that the layout structure in the accessory installation area is more rationalized.

In addition, in order to detect the installation state of the fluid delivery mechanism 200, in this embodiment, the pump main body 100 is also provided with a detecting member. Correspondingly, the connecting base 220 is also provided with an identification member 22151 (as shown in FIG. 4), which cooperates with the detecting member to detect the installation state of the connecting base 220. When the detecting member detects that the fluid delivery mechanism 200 is installed in place, the pump main body 100 may control the anti-disconnecting member 170 to rotate to the locked position to lock the fluid delivery mechanism 200 to the pump main body 100.

As an example, the connecting base 220 may be provided with a mounting groove 2215 (as shown in FIG. 12), and the mounting groove 2215 may be disposed between the first limit groove 2211 and the second limit groove 2212, for example, the mounting groove 2215 is disposed front-to-back and side-by-side with the positioning groove 2213 between the first limit groove 2211 and the second limit groove 2212. The groove opening of the mounting groove 2215 may be oriented toward the pump main body 100. In other words, the mounting groove 2215 extends from one side of the connecting base 220 toward the pump main body 100 toward the other side of the connecting base 220, and the identification member 22151 is disposed within the mounting groove 2215 (as shown in FIG. 4).

The detecting member provided on the pump main body 100 may be a Hall sensor, an infrared sensor, an ultrasonic sensor, a photoelectric sensor, or a microswitch, and the identification member 22151 mounted on the connecting base 220 may be a magnetic member, a shading member, and other components, so that signals such as spacing of the identification member 22151 with respect to the pump main body 100, changes in spacing, changes in position, and the like are detected by the detecting member, in order to monitor the in-position state of the fluid delivery mechanism 200 in real time.

As an example, the detecting member on the pump main body 100 is a Hall sensor and the identification member 22151 on the connecting base 220 is a magnetic member, the magnetic pole direction and magnetic field strength of the magnetic member is detected by the Hall sensor, so that the model number of the fluid delivery mechanism 200 can be identified and whether the fluid delivery mechanism 200 is installed in place can be confirmed.

As an example, the delivery assembly 210 includes a first fluid inlet tube 2121 and a second fluid inlet tube 2122, the valve mechanism 211 has a first inlet 21111a and a second inlet 21111b, and the rotational angle of the reversing groove 21121 on the valve core 2112 for switching among the first open position, the second open position, and the closed position is 60°. That is to say, the rotational angle of the valve core 2112 for switching between the first open position and the second open position, the rotational angle for switching between the first open position and the closed position, and the rotational angle for switching between the second open position and the closed position are all 60°.

Of course, the rotational angle of the reversing groove 21121 on the valve core 2112 for switching among the first open position, the second open position, and the closed position may also be other angular values, and the angular values for switching between the different positions may be inconsistent, which is not limited in this embodiment. It is only necessary to design the control system of the pump main body 100 to ensure that the driving mechanism can drive the switching member 160 to rotate to the corresponding position.

When the fluid delivery mechanism 200 is mounted to the pump main body 100, the valve core 2112 of the valve mechanism 211 on the delivery assembly 210 is in the closed position, and the orientation of the switching member 160 on the pump main body 100 is consistent with the orientation of the reversing groove 21121 when the valve core 2112 is in the closed position, for example, the switching member 160 on the pump main body 100 is horizontally positioned. The anti-disconnecting member 170 on the pump main body 100 may be in the unlocked position, with the orientation of the anti-disconnecting member 170 coinciding with the orientation of the first locating structure (anti-disconnecting hole 22131) on the connecting base 220, e.g., the anti-disconnecting member 170 is also horizontally transverse.

When the fluid delivery mechanism 200 is mounted to the pump main body 100, the switching member 160 on the pump main body 100 extends into the reversing groove
21121 of the valve mechanism 211 on the delivery assembly
210, and the anti-disconnecting member 170 on the pump
main body 100 passes through the anti-disconnecting hole
22131 and is positioned entirely within the opening of the
anti-disconnecting hole 22131. The resilient snap 2214 on
the connecting base 220 is snapped onto the snap base 180
on the pump main body, and the connecting tube 214 of the
delivery assembly 210 is wound around the roller 300. The
detecting member within the pump main body 100 detects a
signal from the identification member 22151 on the con-
necting base 220 to determine the model number of the fluid
delivery mechanism 200 and whether the fluid delivery
mechanism 200 is installed in place.

After determining that the fluid delivery mechanism 200
is installed in place, the control system of the pump main
body 100 controls the driving mechanism to operate, and the
driving mechanism connected to the switching member 160
drives the switching member 160 to rotate 60° clockwise or
counterclockwise as instructed to connect the first fluid inlet
tube 2121 with the fluid outlet tube 213, or to connect the
second fluid inlet tube 2122 with the fluid outlet tube 213.
When driving mechanism drives the switching member 160
to rotate 60°, the switching member 160 drives the anti-
disconnecting member 170 to rotate 90° in the same direc-
tion (or in the opposite direction). Alternatively, an inde-
pendent driving mechanism (connected to the anti-
disconnecting member 170) drives the anti-disconnecting
member 170 to rotate 90° in the same direction (or in the
opposite direction), and the anti-disconnecting member 170
rotates to a position that is perpendicular to the anti-discon-
necting hole 22131 on the connecting base 220, thereby
locking the fluid delivery mechanism 200 to the pump main
body 100.

It should be noted that before the drive unit within the
pump main body 100 drives the roller 300 to rotate, the flow
path within the delivery assembly 210 is blocked by the
squeezing action of the roller 300 on the connecting tube 214
of the delivery assembly 210. Therefore, even if the valve
mechanism 211 is in a state of connecting the first fluid inlet
tube 2121 (the second fluid inlet tube 2122) to the fluid
outlet tube 213, no free-flow is generated within the delivery
assembly 210.

When it is necessary to remove the fluid delivery mecha-
nism 200, the driving mechanism drives the switching
member 160 to turn back to the horizontal transverse state,
and the anti-disconnecting member 170 is also turned back
to the horizontal transverse state driven by the switching
member 160 or by the driving action of the independent
driving mechanism. The anti-disconnecting member 170 is
located completely within the opening of the anti-discon-
necting hole 22131, and the resilient snaps 2214 of the
connecting base 220 are removed from the snap base 180 of
the pump main body 100, so that the fluid delivery mecha-
nism 200 can be removed from the pump main body 100.

Figure 13:
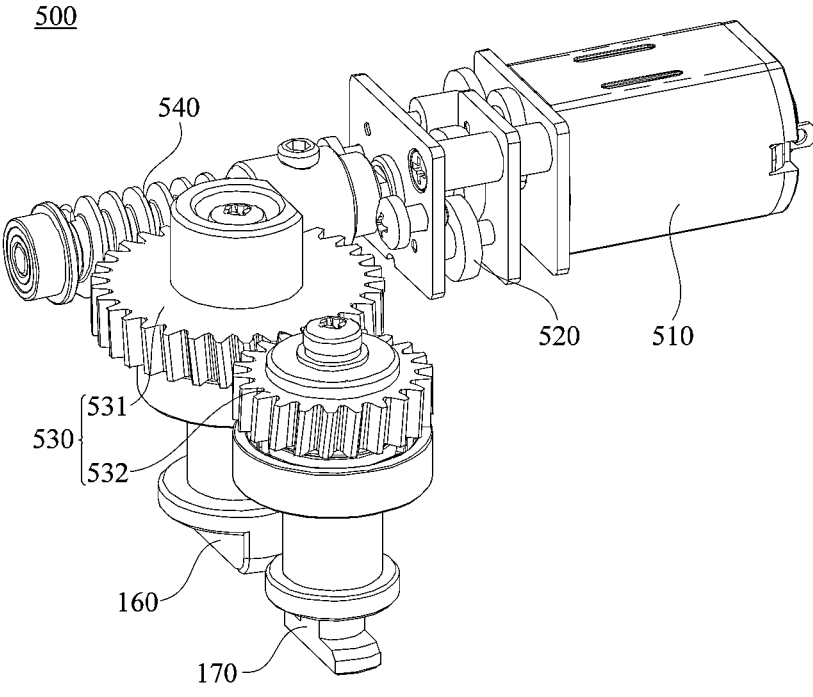
FIG. 13 is a schematic structural diagram of a first driving mechanism provided by embodiments of the invention.

FIG. 13 shows a schematic structural diagram of a first
driving mechanism provided by an embodiment of the
invention. As shown in FIG. 13, in order to drive the
switching member 160 and the anti-disconnecting member
170 to move, in this embodiment, the pump main body 100
is also provided with a first driving mechanism 500, which
may be installed in the pump main body 100 to drive the
switching member 160 and the anti-disconnecting member
170 to move.

The switching member 160 is connected to the first
driving mechanism 500, and the first driving mechanism 500
may drive the switching member 160 to move between at least two positions. Accordingly, the switching member 160
may drive the valve core 2112 to move between at least two
positions so that the valve core 2112 may be moved to either
the conduction position or the cut-off position. As shown in
FIG. 9, when the switching member controls the valve core
2112 to the cut-off position, the circumference of the valve
core 2112 cuts off the connectivity between the inlet 21111
and the outlet 21112 in the valve housing, and the delivery
assembly 210 stops liquid delivery. As shown in FIGS.
10-11, when the switching member 160 controls the valve
core 2112 to the conduction position, the first opening 21122
or the second opening 21123 on the valve core 2112 is in
communication with the inlet 21111 of the valve housing,
such that one of the inlets 21111 of the valve housing is in
communication with the outlet 21112 of the valve housing,
and the delivery assembly 210 can perform liquid delivery.

Similarly, the anti-disconnecting member 170 is con-
nected to the first driving mechanism 500, and the first
driving mechanism 500 may drive the anti-disconnecting
member 170 to move between at least two positions. For
example, the first driving mechanism 500 may drive the
anti-disconnecting member 170 to move to the locked
position to lock the fluid delivery mechanism 200 to the
pump main body 100, and the first driving mechanism 500
may also drive the anti-disconnecting member 170 to move
to the unlocked position to keep the fluid delivery mecha-
nism 200 in a detachable state from the pump main body
100.

It is noted that when the switching member 160 is in the
conduction position, the anti-disconnecting member 170 is
in the locked position to avoid dislodgement of the fluid
delivery mechanism in the infusion state. Besides, when the
switching member 160 is located in the cut-off position, the
anti-disconnecting member 170 is located in the unlocked
position to facilitate removal of the fluid delivery mecha-
nism.

As shown in FIG. 13, in some implementations, the first
driving mechanism 500 may include a first driving member
510 for driving both the switching member 160 and the
anti-disconnecting member 170 to move. In this way, the
cost of the first driving mechanism 500 is low, which can
reduce the overall cost of the nutrient pump. Moreover, only
one first driving member 510 is required to be provided
within the pump main body 100 as a source of driving force
for the switching member 160 and the anti-disconnecting
member 170, and the first driving mechanism 500 occupies
less space as a whole, which facilitates the design of the
structural layout within the pump main body 100, and is
conducive to miniaturization of the nutrient pump.

The first driving member 510 may be a driving motor,
which converts electrical energy into mechanical energy and
outputs a rotational speed and a torque to drive the switching
member 160 and the anti-disconnecting member 170 to
move. Since the driving motor typically outputs a higher
rotational speed and a lower torque, a reducer 520 may also
be provided to be connected to an output end of the driving
motor. The reducer 520 may serve to reduce the rotational
speed and increase the torque, so as to output a suitable
rotational speed and torque to meet the movement require-
ments of the switching member 160 and the anti-discon-
necting member 170.

That is to say, the first driving mechanism 500 may also
include the reducer 520, which is connected to the output
end of the first driving member 510, and is configured to
transmit the power to the switching member 160 and the
anti-disconnecting member 170. The following are all illustrated as examples of the first driving mechanism 500 including the first driving member 510 and the reducer 520.

When the first driving mechanism 500 has only one first driving member 510 for driving both the switching member 160 and the anti-disconnecting member 170, the first driving mechanism 500 may also include a first transmission assembly 530, which is connected to the first driving member 510 in a transmission mode. The switching member 160 and the anti-disconnecting member 170 are connected to an output end of the first transmission assembly 530. The first driving member 510 drives the first transmission assembly 530, and the first transmission assembly 530 drives the switching member 160 and the anti-disconnecting member 170 to move.

The first transmission assembly 530 includes a first transmission member 531 and a second transmission member 532. The first transmission member 531 and the second transmission member 532 are both connected to the first driving member 510. The switching member 160 is connected to an output end of the first transmission member 531, and the anti-disconnecting member 170 is connected to an output end of the second transmission member 532. The first driving member 510 transmits power to the first driving member 531, and the first driving member 531 drives the switching member 160 to move. Similarly, the first driving member 510 transmits power to the second driving member 532, and the second driving member 532 drives the anti-disconnecting member 170 to move.

In some embodiments, the first transmission member 531 may be a gear or rack structure, and the second transmission member 532 may also be a gear or rack structure. The first transmission member 531 and the second transmission member 532 may be connected to the reducer 520, and the reducer 520 transmits power to both the first transmission member 531 and the second transmission member 532. Alternatively, the first transmission member 531 and the second transmission member 532 may be engaged with each other and one of the first transmission member 531 and the second transmission member 532 is connected to the reducer 520, and the reducer 520 transmits power to the transmission member engaged therewith, which then transmits power to the other driving member.

In this embodiment, a worm structure 540 may also be connected to the output end of the reducer 520, and the first transmission assembly 530 is engaged with the worm structure 540. The switching member 160 and the anti-disconnecting member 170 is driven to move through the cooperation of the worm structure 540 and the first transmission assembly 530. As an example, the first transmission member 531 and the second transmission member 532 may be both engaged with the worm structure 540, or, one of the first transmission member 531 and the second transmission member 532 is engaged with the worm structure 540, and the first transmission member 531 and the second transmission member 532 is engaged with each other.

As shown in FIG. 13, as an embodiment, the first transmission member 531 is a gear, the second transmission member 532 is also a gear, the second transmission member 532 is engaged with the first transmission member 531, and the first transmission member 531 is connected to the worm structure 540. The reducer 520 transmits power to the first transmission member 531 through the worm structure 540, and the first transmission member 531 drives the switching member 160 to rotate, thereby realizing switching of the switching member 160 between different positions. At the same time, the first transmission member 531 transmits power to the second transmission member 532 engaged therewith, and the second transmission member 532 drives the anti-disconnecting member 170 to rotate, thereby realizing that the anti-disconnecting member 170 rotates between the switching between the locked position and the unlocked position.

Of course, in other embodiments, when both the first transmission member 531 and the second transmission member 532 are gears, the second transmission member 532 is engaged with the worm structure 540, the first transmission member 531 is engaged with the second transmission member 532, and the power is transmitted to the first transmission member 531 through the second transmission member 532. Alternatively, the first transmission member 531 and the second transmission member 532 may be separately engaged with the worm structure 540, so that the worm structure 540 transmits power to both the first transmission member 531 and the second transmission member 532.

Alternatively, both of the first transmission member 531 and the second transmission member 532 may be rack, and one of the first transmission member 531 and the second transmission member 532 may be engaged with the worm structure 540 and the first transmission member 531 and the second transmission member 532 are engaged with each other. Alternatively, both the first transmission member 531 and the second transmission member 532 may be engaged with the worm structure 540, which is not limited in this embodiment.

When both the first transmission member 531 and the second transmission member 532 are rack, the worm structure 540 may drive the first transmission member 531 and the second transmission member 532 to translate. In this circumstance, the first transmission member 531 may drive the switching member 160 to translate, thereby realizing switching of the switching member 160 between different positions. The second transmission member 532 drives the anti-disconnecting member 170 to translate, thereby realizing switching of the anti-disconnecting member 170 between the locked position and the unlocked position.

Alternatively, one of the first transmission member 531 and the second transmission member 532 may be a gear, and the other may be a rack. Besides, one of the first transmission member 531 and the second transmission member 532 may be engaged with the worm structure 540 and the two are engaged with each other. Alternatively, both of the first transmission member 531 and the second transmission member 532 may be engaged with the worm structure 540, which is not limited in this embodiment.

When one of the first driving member 531 and the second driving member 532 is a gear and the other is a rack, the one of the switching member 160 and the anti-disconnecting member 170 connected to the gear can be rotated under the driving action, and the one of the switching member 160 and the anti-disconnecting member 170 connected to the rack can be translated under the driving action.

Alternatively, in other embodiments, the first transmission assembly 530 may include only one transmission member to which the switching member 160 and the anti-disconnecting member 170 are both connected. For example, the transmission member may be a rack structure, and both the switching member 160 and the anti-disconnecting member 170 are provided with a tooth structure engaged with the rack structure. The transmission member drives both the switching member 160 and the anti-disconnecting member 170 to move.

The following are all illustrated as examples where both the first transmission member 531 and the second transmission member 532 are gears and both are engaged with each other.

As shown in FIG. 13, in practice, within the pump main body 100, the worm structure 540 may be arranged in the planar direction of the pump main body 100. In other words, the first driving member 510, the reducer 520, and the worm structure 540 as a whole may be arranged in the planar direction of the pump main body 100, for example, the worm structure 540 is arranged in parallel with the operating surface of the pump main body 100. The gear shaft of the first driving member 531 and the gear shaft of the second driving member 532 may be parallel to each other and perpendicular to the worm structure 540, so that the switching member 160 connected to the first driving member 531 and the anti-disconnecting member 170 connected to the second driving member 532 are vertically disposed on the operating surface of the pump main body 100.

In some embodiments, the first driving member 510 and the reducer 520 may also be arranged perpendicular to the planar direction of the pump main body 100, e.g., the output end of the reducer 520 extends vertically to the operating surface of the pump main body 100. In this circumstance, when the speed and torque output by the reducer 520 are suitable, instead of connecting the worm structure 540 at the output end of the reducer 520, the first driving member 531 or the second driving member 532 may be directly sleeved around the output end of the reducer 520, and the gear shaft of the first driving member 531 and the gear shaft of the second driving member 532 extends vertically to the operating surface of the pump main body 100. Besides, the switching member 160 and the anti-disconnecting member 170 may be both vertically located on the operating surface of the pump main body 100.

As for the matching setting between the first transmission member 531 and the second transmission member 532 that are engaged with each other, when the rotational angle at which the switching member 160 switches between different positions is the same as the rotational angle at which the anti-disconnecting member 170 switches between the locked position and the unlocked position, the diameters of the first transmission member 531 and the second transmission member 532 can be kept the same, and the first transmission member 531 and the second transmission member 532 rotate at the same speed, and the rotational angle of the switching member 160 is the same as the rotational angle of the anti-disconnecting member 170.

The diameter of the first transmission member 531 and the diameter of the second transmission member 532 may be inconsistent when the rotational angle at which the switching member 160 switches between different positions is inconsistent with the rotational angle at which the anti-disconnecting member 170 switches between the locked position and the unlocked position. The diameter of the first transmission member 531 and the diameter of the second transmission member 532 may be determined by matching the design of the transmission ratios of the first transmission member 531 and the second transmission member 532 based on the relationship between the desired rotational angle of the switching member 160 and the desired rotational angle of the anti-disconnecting member 170.

For example, when the rotational angle at which the switching member 160 switches between different positions is less than the rotational angle at which the anti-disconnecting member 170 switches between the locked position and the unlocked position, the diameter of the first transmission member 531 may be larger than the diameter of the second transmission member 532. On the contrary, when the rotational angle at which the switching member 160 switches between positions is greater than the rotational angle at which the anti-disconnecting member 170 switches between the locked position and the unlocked position, the diameter of the first transmission member 531 may be smaller than the diameter of the second transmission member 532.

By designing the size of the diameters of the first transmission member 531 and the second transmission member 532, it can be ensured that when the switching member 160 is located in the conduction position, the anti-disconnecting member 170 is located in the locked position, so as to avoid dislodgement of the fluid delivery mechanism in the infusion state. Moreover, it may be ensured that the anti-disconnecting member 170 is in the unlocked position when the switching member 160 is in the cut-off position to facilitate removal of the fluid delivery mechanism.

In addition to relying on one first driving member 510 to simultaneously drive the switching member 160 and the anti-disconnecting member 170 to move, two first driving members 510 may be provided to drive the switching member 160 and the anti-disconnecting member 170 to move, respectively. In other words, the first driving mechanism 500 may include two first driving members 510, one of the two first driving members 510 is connected to the switching member 160 and drives the switching member 160 to move, and the other of the two driving members is connected to the anti-disconnecting member 170 and drives the anti-disconnecting member 170 to move.

By setting the two first driving members 510 to drive the switching member 160 and the anti-disconnecting member 170 respectively, the driving method of the switching member 160 and the anti-disconnecting member 170 is made simpler, and the respective driving structures need to be designed only according to the respective required displacements (e.g., rotational angles) of the switching member 160 and the anti-disconnecting member 170, and there is no need to consider the transmission ratio design when the transmission between the switching member 160 and the anti-disconnecting member 170.

Similar to the aforementioned simultaneous driving of the switching member 160 and the anti-disconnecting member 170 by means of one first driving member 510, when the switching member 160 and the anti-disconnecting member 170 are driven separately by means of two first driving members 510, each of the two first driving members 510 may include a driving motor and a reducer 520. Furthermore, when both the switching member 160 and the anti-disconnecting member 170 are driven by means of a gear or a rack, a worm structure 540 may connected to the output end of the reducer 520, with the gear or the rack connected to the switching member 160 being engaged with one of the worm structures 540, and the gear or the rack connected to the anti-disconnecting member 170 being engaged with the other worm structure 540.

As an example, both the switching member 160 and the anti-disconnecting member 170 are driven by gears, both of the worm structures 540 connected to the two first driving members 510 may be arranged in the planar direction of the pump main body 100, e.g., both of the worm structures 540 are parallel to the operating surface of the pump main body 100, and shaft structures of the gears connected to the switching member 160, and shaft structures of the gears connected to the anti-disconnecting member 170 may both be perpendicular to the worm structure 540, so that both the switching member 160 and the anti-disconnecting member 170 are both erected on the operating surface of the pump main body 100.

Alternatively, the two first driving members 510 and the reducers 520 connected thereto may be arranged perpendicular to the planar direction of the pump main body 100, for example, the output ends of both reducers 520 extends vertically to the operating surface of the pump main body 100. In this circumstance, when the rotational speed and torque output by the two reducers 520 are suitable, instead of connecting the worm structure 540 at the output ends of the two reducers 520, the switching member 160 and the anti-disconnecting member 170 may be directly connected to the output ends of the corresponding reducers 520, respectively, to make the switching member 160 and the anti-disconnecting member 170 both vertically located on the operating surface of the pump main body 100.

Figure 14:
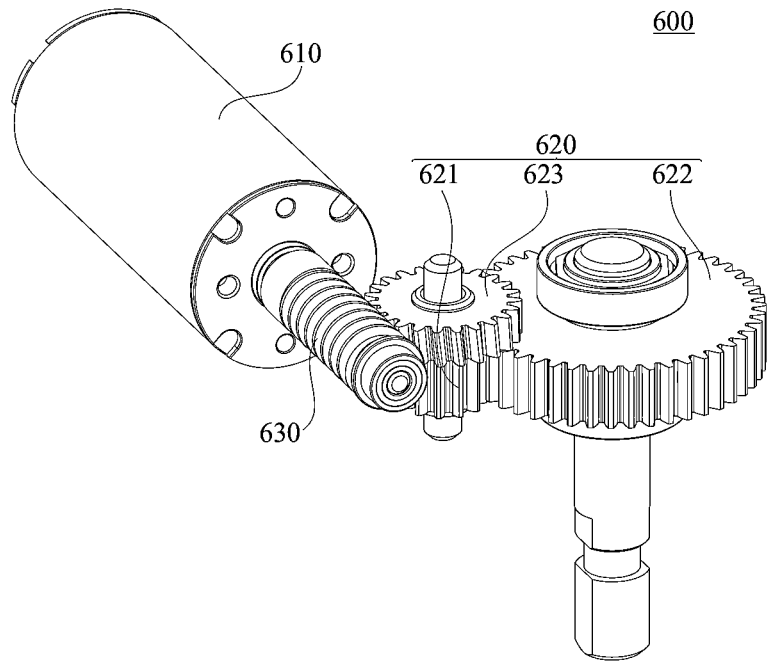
FIG. 14 is a schematic structural diagram of a second driving mechanism provided by an embodiment of the invention.

FIG. 14 shows a schematic structural diagram of a second driving mechanism provided by an embodiment of the invention. As shown in FIG. 14, in order to drive the pump roller 300 to rotate, in this embodiment, the pump main body 100 is also provided with a second driving mechanism 600, and the second driving mechanism 600 may also be mounted in the pump main body 100. The pump roller 300 is connected to an output end of the second driving mechanism 600, and the pump roller 300 is driven to rotate by the second driving mechanism 600.

In some embodiments, the second driving mechanism 600 may include a second driving member 610 and a second transmission assembly 620. The second transmission assembly 620 is connected to the second driving member 610 in a transmission mode. An output end of the second transmission assembly 620 extends outside the pump main body 100, and the pump roller 300 is connected to the output end of the second transmission assembly 620. The second driving member 610 is configured to provide a driving force and transmit the driving force to the second transmission assembly 620 to drive the pump roller 300 to rotate through the second transmission assembly 620.

As an example, the output end of the second drive assembly 620 may be designed as a structural form of a driving shaft, and the output end of the second driving member 532 serves as a pump spindle of the pump main body 100. The pump roller 300 may be sleeved around the pump spindle, and the pump spindle rotates to drive the pump roller 300 to synchronously rotate.

The second driving member 610 may also be a driving motor, and the driving motor converts electrical energy into mechanical energy to output a rotational speed and torque, and thus, drives the second transmission assembly 620 in motion. The second transmission assembly 620 transmits the power to the pump roller 300 to drive the pump roller 300 to rotate.

As shown in FIG. 14, the second driving mechanism 600 may also drive the pump roller 300 to rotate by means of a gear transmission. In an embodiment, the second transmission assembly 620 may include a first gear 621 and a second gear 622. The first gear 621 is connected to the second driving member 610 in a transmission mode, and the second gear 622 is engaged with the first gear 621. An output end of the second gear 622 is a pump spindle, and the pump roller 300 is sleeved around the pump spindle.

In this circumstance, the drive motor output of the second drive member 610 typically has a higher rotational speed and a lower torque, and in order to allow the pump spindle on the second gear 622 to rotate at a suitable speed, the second drive assembly 620 serves to reduce the rotational speed and increase the torque. Thus, the diameter of the first gear 621 may be smaller than the diameter of the second gear 622 to reduce the rotational speed of the pump spindle.

Moreover, in this embodiment, instead of setting the reducer 520 at the output end of the second driving member 610, the second transmission assembly 620 may be directly connected to the output end of the second driving member 610. In this circumstance, in order to reduce the rotational speed of the second driving member 610 to a suitable rotational speed, a third gear 623 may be added. That is to say, the second drive assembly 620 may also include the third gear 623, which may be coaxially disposed with the first gear 621, and the third gear 623 is connected to the output end of the second driving member 610 in a transmission mode.

The diameter of the third gear 623 may be larger than the diameter of the first gear 621. In this way, compared to the first gear 621 being directly connected to the output end of the second driving member 610 in a transmission mode, the rotational speed of the gear shaft common to the third gear 623 and the first gear 621 can be reduced by setting the third gear 623 to be connected to the output end of the second driving member 610 in a transmission mode, and then, by making the drive between the first gear 621 of a smaller diameter and the second gear 622 of a largest diameter, the rotational speed of the pump spindle on the second gear 622 to be reduced to a suitable range.

Of course, if the output end of the second driving member 610 is provided with a reducer 520, it is also possible to reduce the rotational speed without additionally providing the third gear 623. The first gear 621 may be directly connected to the output end of the reducer 520 by a transmission, or, even, without providing the first gear 621, the second gear 622 may be directly to the output end of the reducer 520 in a transmission mode.

As shown in FIG. 14, similar to the first driving mechanism 500, when the second driving member 610 is arranged in the planar direction of the pump main body 100, a worm structure may also be connected to the output end of the second driving member 610. For the sake of illustration, the worm structure connected to the second driving member 610 is defined as a transmission worm 630 in this embodiment. The gear shafts of each gear in the second transmission assembly 620 may be parallel to each other and all perpendicular to the transmission worm 630 so that the pump spindle on the second gear 622 extends vertically over the operating surface of the pump main body 100 for the pump roller 300 to be connected thereto.

Alternatively, the second driving member 610 may be arranged perpendicular to the planar direction of the pump main body 100, for example, the output end of the second driving member 610 extends vertically to the operating surface of the pump main body 100. In this case, instead of connecting the transmission worm 630 to the output end of the second driving member 610 and setting the third gear 623, the first gear 621 can be directly sleeved around the output end of the second driving member 610, and the pump spindle on the second gear 622 engaged with the first gear 621 extends vertically on the operating surface of the pump main body 100 so as to facilitate the connection of the pump roller 300 thereto.

When the nutrient pump 1 is in use, the valve core 2112 of the control valve 211 on the delivery assembly 210 is in the cut-off position before the fluid delivery mechanism 200 is mounted to the pump main body 100, and the switching member 160 on the pump main body 100 is oriented in the same way as the orientation of the reversing groove 21121 when the valve core 2112 is in the cut-off position, e.g., the switching member 160 on the pump main body 100 is horizontally transverse. The anti-disconnecting member 170 on the pump main body 100 may be in the unlocked position, and the orientation of the anti-disconnecting member 170 corresponds to the orientation of the anti-disconnecting hole 22131 in the connecting base 220, e.g., the anti-disconnecting member 170 is also horizontally transverse.

When the fluid delivery mechanism 200 is mounted to the pump main body 100, the switching member 160 on the pump main body 100 extends into the reversing groove 21121 of the control valve 211 on the delivery assembly 210, and the anti-disconnecting member 170 on the pump main body 100 passes through the anti-disconnecting hole 22131 and is positioned entirely within the opening of the anti-disconnecting hole 22131. The resilient snap 2214 on the connecting base 220 is snapped into the snap base 180, and the connecting tube 214 of the delivery assembly 210 is wound around the pump roller 300. The pump main body 100 detects an identification signal from the connecting base 220, and determines the model number of the fluid delivery mechanism 200 and whether the fluid delivery mechanism 200 is installed in place.

The pump main body 100 receives an instruction to select a certain fluid inlet tube 212 (e.g., the first fluid inlet tube 2121) for fluid delivery: before starting the fluid delivery, the first driving mechanism 500 on the pump main body 100 operates, and the first driving member 510 operates to drive the switching member 160 and the valve core 2112 of the control valve 211 to move to a certain connected position (e.g., the first connected position), and drives the anti-disconnecting member 170 to move to the locked position at the same time. Afterwards, the second driving mechanism 600 is activated and the second driving member 610 operates to drive the pump roller 300 to rotate and start the infusion.

It should be noted that before the second driving mechanism 600 drives the pump roller 300 to rotate, the fluid pathway within the delivery assembly 210 is blocked by the squeezing action of the pump roller 300 on the connecting tube 214 of the delivery assembly 210. Therefore, even if the control valve 211 is in the state of connecting a certain fluid inlet tube 212 to a fluid outlet tube 213, a free-flow will not be generated within the delivery assembly 210.

The pump main body 100 receives an instruction to select another fluid inlet tube 212 (e.g., the second fluid inlet tube 2122) for fluid infusion: before starting the fluid infusion, the first driving mechanism 500 on the pump main body 100 operates, and the first driving member 510 operates to drive the switching member 160 and the valve core 2112 of the control valve 211 to move to another connecting position (e.g., the second connecting position), and drive the anti-disconnecting member 170 to move to the locked position at the same time. Afterwards, the second driving mechanism 600 is activated and the second driving member 610 operates to drive the pump roller 300 to rotate and start the infusion.

It should be noted that when the switching member 160 drives the valve core 2112 of the control valve 211 to move between different connecting positions, the orientation of the anti-disconnecting member 170 also moves. However, when the switching member 160 drives the valve core 2112 of the control valve 211 to move to any connecting position, the anti-disconnecting member 170 is always in the locked position after the movement.

The pump main body 100 receives an instruction to stop the infusion: the second driving member 610 firstly stops operating to stop the rotation of the pump roller 300. Then, the first driving member 510 operates to drive the switching member 160 to move to the initial position, and the switching member 160 drives the valve core 2112 of the control valve 211 back to the cut-off position, and drives the anti-disconnecting member 170 back to the initial unlocked position at the same time. At this time, the fluid delivery mechanism 200 can be removed from the pump main body 100.

In the description of the invention, it is to be understood that the terms "center", "longitudinal", "lateral", "length", "width", "thickness", "up", "down", "front", "back', "left", "right", "vertical", "horizontal", "top", "bottom", "inside", "outside", etc. indicate orientations or positional relationships based on those shown in the accompanying drawings, and are intended only to facilitate the description of the invention and to simplify the description, and are not intended to indicate or imply that the device or element referred to must have a particular orientation, be constructed and operated in a particular orientation, and therefore are not to be construed as a limitation of the invention.

Finally, it should be noted that the above embodiments are only used to illustrate the technical solutions of the invention, not to limit the same. Although the invention has been described in detail with reference to the foregoing embodiments, a person of ordinary skill in the art should understand that it is still possible to make modifications to the technical solutions recorded in the foregoing embodiments, or to make equivalent substitutions for some or all of the technical features therein; and such modifications or substitutions do not take the essence of the corresponding technical solutions out of the scope of the technical solutions of the embodiments of the invention.

The invention claimed is:

1. A fluid delivery mechanism, comprising:
   a delivery assembly comprising a flow path and a valve mechanism provided in the flow path; and
   a connecting base, the delivery assembly being mounted on the connecting base;
   wherein the valve mechanism comprises a valve housing and a valve core removably connected to the valve housing;
   the valve housing comprises an outlet and at least one inlet; and
   the valve core includes a hollow structure within the valve core and directly connecting to both a first opening and a second opening that are configured on a circumference of the valve core, and the hollow structure is further in communication with the outlet of the valve housing to provide a fluid passage with the valve housing;
   wherein the valve core is rotatable in a first direction to make one of the first opening and the second opening in communication with one of the at least one inlet, and
   the at least one inlet include a first inlet and a second inlet, and when the valve core is in an initial position, the first opening is configured in line with the first inlet on one side of the outlet, and the second opening is configured in line with the second inlet on the other side of the outlet.

2. The fluid delivery mechanism of claim 1, wherein the valve core is rotatable in the first direction to make the first inlet in communication with the first opening and rotatable in a second direction to make the second inlet communication with the second opening; wherein the first direction is opposite to the second direction.

3. The fluid delivery mechanism of claim 2, wherein the first inlet and the second inlet are disposed side by side on the valve housing.

4. The fluid delivery mechanism of claim 1, wherein the valve core is provided with a reversing groove.

5. The fluid delivery mechanism of claim 1, further comprising an outlet tube and at least one inlet tube, wherein each of the at least one inlet tube is connected to a corresponding inlet on the valve mechanism and the fluid outlet tube is connected to the outlet of the valve mechanism.

6. The fluid delivery mechanism of claim 1, wherein the connecting base is provided with a first locking structure, and the valve mechanism is detachably connected to the first locking structure.

7. The fluid delivery mechanism of claim 1, further comprising a tube connector, wherein the tube connector is provided on the flow path, the connecting base is provided with a second locking structure, and the tube connector is detachably connected to the second locking structure.

8. A nutrient pump, comprising:
a pump main body; and
a fluid delivery mechanism, the fluid delivery mechanism being detachably connected to the pump main body and comprising:
    a delivery assembly comprising a flow path and a valve mechanism provided in the flow path; and
    a connecting base, the delivery assembly being mounted on the connecting base;
    wherein the valve mechanism comprises a valve housing and a valve core removably connected to the valve housing;
the valve housing comprises an outlet and at least one inlet; and
the valve core includes a hollow structure within the valve core and directly connecting to both a first opening and a second opening that are configured on a circumference of the valve core, and the hollow structure is further in communication with the outlet of the valve housing to provide a fluid passage with the valve housing;
    wherein the valve core is rotatable in a first direction to make one of the first opening and the second opening in communication with one of the at least one inlet, and
the at least one inlet include a first inlet and a second inlet, and when the valve core is in an initial position, the first opening is configured in line with the first inlet on one side of the outlet, and the second opening is configured in line with the second inlet on the other side of the outlet.

9. The nutrient pump of claim 8, wherein
the valve core is rotatable in the first direction to make the first inlet in communication with the first opening and rotatable in a second direction to make the second inlet communication with the second opening; wherein the first direction is opposite to the second direction.

10. The nutrient pump of claim 8, wherein the pump main body is provided with a switching member, and the switching member is capable of extending into a reversing groove of the valve core of the valve mechanism to drive the valve core.

11. The nutrient pump of claim 8, wherein the pump main body is provided with an anti-disconnecting member, and the anti-disconnecting member is movable to a locked position or an unlocked position;

when the anti-disconnecting member is in the locked position, the anti-disconnecting member is connected to the connecting base; when the anti-disconnecting member is in the unlocked position, the anti-disconnecting member is disengaged from the connecting base.

12. The nutrient pump of claim 8, wherein the pump main body is provided with a fixing structure, and the fixing structure is detachably connected to a second positioning structure of the connecting base.

13. The nutrient pump of claim 8, wherein the pump main body is provided with a detecting member, and the connecting base is provided with an identification member; the detecting member is cooperated with the identification member to detect an installation state of the connecting base.

14. A nutrient pump, comprising:
a pump main body;
a first driving mechanism;
a switching member; and
an anti-disconnecting member;
wherein the first driving mechanism, the switching member and the anti-disconnecting member are provided on the pump main body; the first driving mechanism is connected to the switching member to drive the switching member to move between at least two positions to control a fluid conduction cut-off state of a fluid delivery mechanism; and the first driving mechanism is connected to the anti-disconnecting member to drive the anti-disconnecting member to move between at least two positions,
wherein the first driving mechanism comprises a first driving member, and the first driving member is configured to drive both the switching member and the anti-disconnecting member to move, and
wherein the first driving mechanism further comprises a first transmission assembly; the first transmission assembly is connected to the first driving member in a transmission mode, and the switching member and the anti-disconnecting member are both connected to an output end of the first transmission assembly.

15. The nutrient pump of claim 14, wherein the first transmission assembly comprises a first transmission member and a second transmission member, the switching member is connected to an output end of the first transmission member, and the anti-disconnecting member is connected to an output end of the second transmission member.

16. The nutrient pump of claim 15, wherein the first driving mechanism further comprises a worm structure; the worm structure is connected to the first driving member in a transmission mode, and the first driving member and second driving member are both engaged with the worm structure; or
one of the first driving member and the second driving member is engaged with the worm structure, and the first driving member is engaged with the second driving member.

17. The nutrient pump of claim 14, wherein the first driving mechanism comprises two first driving members, one of the two first driving members is connected to the switching member, and the other of the two first driving members is connected to the anti-disconnecting member.

18. The nutrient pump of claim 14, wherein the pump main body is further provided with a second driving mechanism, which is configured to drive a pump roller to rotate.

\* \* \* \* \*